(12) United States Patent
Sanyal et al.

(10) Patent No.: US 8,288,513 B2
(45) Date of Patent: Oct. 16, 2012

(54) DEFINED CELL CULTURING SURFACES AND METHODS OF USE

(75) Inventors: Suparna Sanyal, Tewksbury, MA (US); Deepa Saxena, Framingham, MA (US); Susan Xiuqi Qian, Concord, MA (US); Elizabeth Abraham, Andover, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 500 days.

(21) Appl. No.: 12/508,661

(22) Filed: Jul. 24, 2009

(65) Prior Publication Data

US 2010/0021998 A1 Jan. 28, 2010

Related U.S. Application Data

(60) Provisional application No. 61/083,570, filed on Jul. 25, 2008, provisional application No. 61/085,044, filed on Aug. 13, 2008.

(51) Int. Cl.
*C07K 17/00* (2006.01)
(52) U.S. Cl. ........ 530/350; 530/353; 427/447; 427/488; 427/533; 264/483
(58) Field of Classification Search .................. None
See application file for complete search history.

(56) References Cited

U.S. PATENT DOCUMENTS

| 5,449,383 A | 9/1995 | Chatelier et al. | |
| 2006/0251693 A1* | 11/2006 | Short et al. | 424/422 |

FOREIGN PATENT DOCUMENTS

| EP | 1 857 545 A1 | 11/2007 |
| WO | 89/11500 A1 | 11/1989 |
| WO | 00/29548 A2 | 5/2000 |
| WO | 03/035850 A1 | 5/2003 |
| WO | 2007/113587 A2 | 10/2007 |

OTHER PUBLICATIONS

BD Biosciences Labware, "Multiwell TC Plates—6 Well", Document No. LSR00001, Rev. 2; pp. 1-2; [retrieved on Apr. 16, 2010], XP-002578177.
Konno, T. et al., "Culture of Mouse Embryonic Stem Cells on Photoimmobilized Polymers", Journal of Bioscience and Bioengineering, 2006; vol. 102, No. 4, pp. 304-310.
Derda, R. et al., "Defined Substrates for Human Embryonic Stem Cell Growth Identified from Surface Arrays", ACS Chemical Biology, 2007, vol. 2, No. 5, pp. 347-355, XP007912131.
Alberti, K. et al., "Functional Immobilization of signaling proteins enables control of stem cell fate", Nature Methods, Jul. 2008, vol. 5, No. 7, pp. 645-650, XP-002578176.

* cited by examiner

*Primary Examiner* — Jim Ketter
(74) *Attorney, Agent, or Firm* — Hoffman & Baron, LLP

(57) ABSTRACT

In one aspect, there is provided a cell culturing substrate including: a cell culture surface having a film attached thereto, wherein the film includes one or more plasma polymerized monomers; and a coating on the film-coated surface, the coating deposited from a coating solution comprising one or more extracellular matrix proteins and an aqueous solvent, where the total extracellular matrix protein concentration in the coating solution is about 1 ng/mL to about 1 mg/mL.

15 Claims, 15 Drawing Sheets

ECTODERM

NESTIN/DAPI

ECTODERM $\beta$-TUBULIN 3/DAPI

MESODERM

α-SM ACTIN/DAPI

MESODERM

BRACHYURY/DAPI

CONCENTRATION OF hFN COATING (μg/mL) SHOWN IN WHITE BOX ABOVE

TC

TC+P-ORNITHINE & LAMININ

BD PRIMEX 1

BD PRIMEX 1+FIBRONECTIN

DEFINED CELL CULTURING SURFACES AND METHODS OF USE

CROSS-REFERENCE TO RELATED APPLICATIONS

This application claims priority to U.S. Provisional Patent Application No. 61/083,570, filed Jul. 25, 2008, and to U.S. Provisional Patent Application No. 61/085,044, filed Aug. 13, 2008, the entire contents of both applications being incorporated by reference herein in their entireties.

FIELD OF THE INVENTION

This invention relates to defined surfaces for culturing cells. More particularly, the present invention provides methods and materials for culturing embryonic stem cells and other adult stem cells on defined cell culture surfaces.

BACKGROUND OF THE INVENTION

Human embryonic stem (hES) cells typically require a substrate and culture medium to maintain indefinite self-renewal and pluripotency characteristics. The most common substrates for culturing hES cells are monolayers of inactivated fibroblast feeder cells grown on tissue culture (TC) polystyrene surface or TC culturing vessels coated with an extracellular matrix (ECM), for example BD Matrigel™-coated TC culturing vessels. Both of these substrates are poorly defined and introduce a high degree of experimental variability. Since hES cells are thought to have a significant potential implication in furthering knowledge of developmental biology, drug discovery and may play an important role in future clinical applications, it is important to identify conditions for culturing these cells on defined surfaces.

SUMMARY OF THE INVENTION

In one aspect, there is provided a cell culturing substrate including: a cell culture surface having a film attached thereto, wherein the film includes one or more plasma polymerized monomers; and a coating on the film-coated surface, the coating deposited from a coating solution comprising one or more extracellular matrix proteins and an aqueous solvent, where the total extracellular matrix protein concentration in the coating solution is about 1 ng/mL to about 1 mg/mL.

In other aspects, there is provided a method of preparing a cell culturing substrate including: providing a cell culture surface; plasma polymerizing a film onto the surface to form a film-coated surface, wherein the plasma polymerizing utilizes one or more monomers; and introducing a coating solution to the film-coated surface to form a cell culture substrate, the coating solution including one or more extracellular matrix proteins and an aqueous solution, wherein the total extracellular matrix protein concentration in the coating solution is about 1 ng/mL to about 1 mg/mL.

In aspects, there is provided a method of culturing stem cells including: providing a cell culturing substrate; applying a suspension of stem cells to the cell culturing substrate; incubating the suspension of stem cells on the cell culturing substrate at 5% $CO_2$ in humidified air at 37° C.; and permitting the stem cells to attach to the cell culturing substrate, wherein the attached cells remain in a predominately undifferentiated state. Unless differentiation is pinduced using specific differentiation factors in media (E.G. EXAMPLE 10)

Advantageously, with subject to the invention, a cell culturing substrate may be provided that has good attachment characteristics for stem cells with favorable avoidance of stem cell differentiation.

BRIEF DESCRIPTION OF THE FIGURES

FIG. 7 Graphical representation and pictoral of plates demonstrating concentrating of hFN in the coating.

DETAILED DESCRIPTION OF THE INVENTION

Figure 1A:
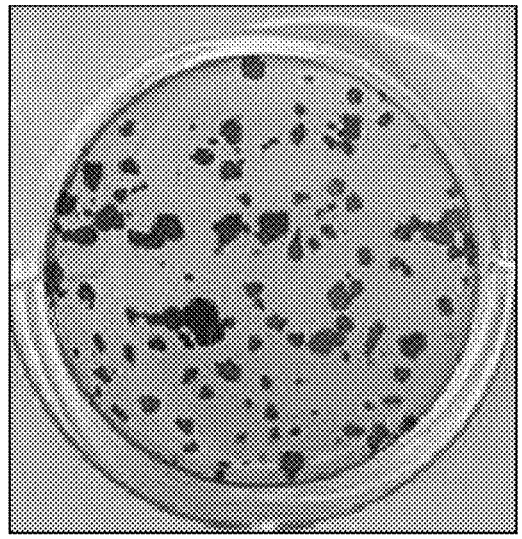
FIG. 1 depicts comparative colony attachment of crystal violet stained human embryonic stem (hES) cells seeded on various substrates: tissue culture (TC)-treated polystyrene plates coated with extracellular matrix, more specifically, Matrigel™, a complex mixture of extracellular matrix proteins (FIG. 1A), TC treated polystyrene plates coated with human fibronectin (FIG. 1B); and plasma polymerized plates coated with human fibronectin (FIG. 1C) and growth media.

A defined cell culturing substrate is provided for propagating stem cells in an undifferentiated state and maintaining their self-renewal and pluripotency characteristics for extended periods of time in culture. The defined culture surface of the present invention promotes more efficient attachment and expansion of human embryonic as well as mesenchymal and neural stem cells in an undifferentiated state, as compared to standard culture substrates such as tissue culture-treated surfaces. In some embodiments, hES cells, human bone marrow derived mesenchymal stem cells and hESC-derived neuronal stem cells may be propagated from the defined cell culture surface. In some embodiments, the defined cell culture surface is xeno-free.

A cell culture surface is provided. Preferably, the cell culture surface is defined on a culture vessel. The cell culture surface may be defined over media found within a cell culture vessel or other structure. Material for the cell culture surface may include plastic (e.g. polystyrene, acrylonitrile butadiene styrene, polycarbonate); glass; microporous filters (e.g., cellulose, nylon, glass fiber, polyester, and polycarbonate); materials for bio-reactors used in batch or continuous cell culture or in genetic engineering (e.g., bioreactors), which may include hollow fiber tubes or micro carrier beads; polytetrafluoroethylene (Teflon®), ceramics and related polymeric materials. Any material listed above or others are suitable for use in the present invention. The material for the cell culture surface may be selected from: cellulose, polystyrene, polycarbonate, polytetrafluoroethylene, nylon, glass, polyethyleneterephthalate, polymethylpentane, polypropylene, polyethylene and combinations thereof. These materials may be porous or non-porous.

For illustrative purposes, reference shall be made herein to a cell culture or culture vessel. It is to be understood that the invention herein may be utilized on various cell culture surfaces including, but not limited to surfaces defined on media found in cell culture vessels, such as microbeads, microporous filters or other filtration or binding media. Preferably, the cell culture surface is formed of polystyrene.

It is contemplated that any culture vessel that is useful for adherent cultures may be used. Preferred cell culture vessel configurations contemplated by the present invention include multiwell plates (such as 6-well, 12-well and 24-well plates), dishes (such as petri dishes), test tubes, culture flasks, roller bottles, tube or shaker flasks, and the like.

The cell culture surface is coated with a plasma polymerized film. The source of the plasma polymerization is one or more monomers. Useful polymerizable monomers may include unsaturated organic compounds such as olefinic amines, halogenated olefins, olefinic carboxylic acids and carboxylates, olefinic nitrile compounds, oxygenated olefins and olefinic hydrocarbons. In some embodiments, the olefins may include vinylic and allylic forms. In other embodiments, cyclic compounds such as cyclohexane, cyclopentane and cyclopropane may be used.

As will be recognized by those skilled in the art, various plasma polymerization techniques may be utilized to deposit the one or more monomers onto the cell culture surfaces. Preferably, a positively charged polymerized film is deposited on the surfaces. As will be appreciated by one skilled in the art, the plasma polymerized surface may have a negative charge depending on the proteins to be used therewith. Amine is preferably used as the monomer source of the polymer. In some embodiments, the plasma polymerized monomer is made using plasma sources to generate a gas discharge that provides energy to initiate polymerization of gaseous monomers, and allows a thin polymer film to deposit on a culture vessel. Cyclic compounds may be utilized which may include gas plasmas by glow discharge methods. Derivatives of these cyclic compounds, such as 1,2- diaminocyclohexane for instance, are also commonly polymerizable in gas plasmas.

The coating composition preferably includes a single type of extracellular matrix protein. In some preferred embodiments, the coating composition includes fibronectin, particularly for use with culturing stem cells. For example, a suitable coating composition may be prepared by diluting human fibronectin, such as human fibronectin sold by Becton, Dickinson & Co. of Franklin Lakes, N.J. (BD) (Cat#354008), in Dulbecco's phosphate buffered saline (DPBS) to a protein concentration of 5 µg/mL to about 200 µg/mL.

Mixtures of polymerizable monomers may be used. Additionally, polymerizable monomers may be blended with other gases not generally considered as polymerizable in themselves, examples being argon, nitrogen and hydrogen.

In one aspect of the invention, the polymer includes an amine co-polymer (polymerization of two or more monomers). The co-polymer is prepared by the plasma polymerization of an organic amine with a saturated (alkane) or unsaturated (alkene, diene or alkyne) hydrocarbon. The hydrocarbon would be of up to 20 carbons (but more usually of 4 to 8). Examples of alkanes are butane, pentane and hexane. Examples of alkenes are butene and pentene. An example of a diene is 1-7 octadiene. The co-monomer may also be aromatic-containing e.g. styrene.

Plasma polymerization may be carried out as a copolymer polymerization of two components using any ratio of amine:hydrocarbon. Preferably, the amine:hydrocarbon ratio for the co-plasma polymerization is between the limits of 100 (amine):0(hydrocarbon) to 20 (amine):80 (hydrocarbon) and any ratio between these limits.

With a plasma polymerized film coating deposited on the cell culture surfaces, a coating composition is immobilized on the film-coated surface with a coating composition. The coating composition may include one or more extracellular matrix (ECM) proteins and an aqueous solvent. The term "extracellular matrix" is recognized in the art. Its components include one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin. Other extracellular matrix proteins are described in Kleinman et al., *J. Biometer. Sci. Polymer Edn.*, 5: 1-11, (1993), herein incorporated by reference. It is intended that the term "extracellular matrix" encompass a presently unknown extracellular matrix that may be discovered in the future, since its characterization as an extracellular matrix will be readily determinable by persons skilled in the art.

In some aspects, the total protein concentration in the coating composition may be about 1 ng/mL to about 1 mg/mL. In some preferred embodiments, the total protein concentration in the coating composition is about 1 µg/mL to about 300

μg/mL. In more preferred embodiments, the total protein concentration in the coating composition is about 5 μg/mL to about 200 μg/mL.

The extracellular matrix (ECM) proteins useful in the coating may be of natural origin and purified from human or animal tissues. Alternatively, the ECM proteins may be genetically engineered recombinant proteins or synthetic in nature. The ECM proteins may be a whole protein or in the form of peptide fragments. Examples of ECM protein coatings that may be useful in the coating include laminin, collagen I, collagen IV, fibronectin and vitronectin.

In some embodiments, the coating composition is xeno-free, in that the proteins are only of human origin. This may be desired for certain research applications.

In some embodiments, the coating composition includes synthetically generated peptide fragments of fibronectin or recombinant fibronectin.

In still further embodiments, the coating composition includes a mixture of at least fibronectin and vitronectin.

In some other embodiments, the coating composition preferably includes laminin.

The aqueous solvent useful in preparing the coating compositions may be water or a buffer, such as phosphate buffered saline, specifically Dulbecco's phosphate buffered saline (DPBS), or a cell culture media, for example. In some embodiments, DMEM, KO/DMEM, DMEM/F12, RPMI, or other cell culture media known in the art, are suitable for use as the aqueous solvent used to prepare the coating. Suitable aqueous solvent diluents can include any cell culture medium, which provides a condition that is compatible with embryonic cell culture, and preferably maintains the cells in a self-renewing and an undifferentiated state until directed into a particular cell type in vitro. Such media may be obtained commercially, for example, from StemCell Technologies, Inc. (Vancouver, BC, Canada), Invitrogen Corporation (Carlsbad, Calif.) or Sigma-Aldrich (St. Louis, Mo.).

The coating composition preferably includes a single type of extracellular matrix protein. In some preferred embodiments, the coating composition includes fibronectin, particularly for use with culturing stem cells. For example, a suitable coating composition may be prepared by diluting human fibronectin, such as human fibronectin sold by Becton, Dickinson & Co. of Franklin Lakes, N.J. (BD) (Cat#354008), in Dulbecco's phosphate buffered saline (DPBS) to a protein concentration of 5 μg/mL to about 200 μg/mL.

In some other embodiments, the coating composition preferably includes laminin. For example, a suitable coating composition may be prepared by diluting laminin (Sigma-Aldrich (St. Louis, Mo.); Cat#L6274 and L2020) in Dulbecco's phosphate buffered saline (DPBS) to a protein concentration of 5 μg/ml to about 200 μg/ml.

In some embodiments, the coating composition has a pH of between about 7.0 to about 8.5. The pH may be maintained with any buffering component capable of maintaining the composition within the pH range of about 7.0 to 8.5. Potential buffer systems in this range include, but are not limited to, diethanolamine, triethanolamine, (1,3-bis(tris[Hydroxymethyl]methylamino)propane); 3-[N,N-bis(2-Hydroxyethyl) amino]-2-hydroxypropanesulfonic acid: DIPSO; (N-[2-Hydroxyethyl]piperazine-N'-[-4-butanesulfonic acid] HEPBS); (N-(4-(2-hydroxyethyl-1-piperazineethanesulfonic acid: HEPES); 3-(N-Morpholino)butane sulfonic acid: MOBS); (Piperazine-N,N'-bis[2-hydroxypropanesulfonic acid: POPSO); (N-tris(Hydroxymethyl)methyl-3-aminopropanesulfonic acid: TAPS; 3-(N-tris[Hydroxymethyl]methylamino)-2-hydroxypropanesulfonic acid: TAPSO); (N-tris (Hydroxymethyl)methyl-2-aminoethanesulfonic acid: TES; (N-tris(Hydroxymethyl)methylglycine: Tricine; N-ethylmorpholine, dimethylleucylglycine, sodium 5:5-diethyl barbituate and 2 amino, 2 methyl-1:3 propanediol.

The coating compositions used to prepare the culturing system of the present invention can include various components, which can affect the accessibility of growth factors in the coating to cells and/or which assist in cell adhesion and/or which affect the structure of the proteins in the coating. These components may include, but are not limited to, salts, diluents, heparan sulfate proteoglycans.

A wide variety of other materials, may be included in the coating on the substrate. These include, but are not limited to, cells, antibodies, enzymes, receptors, growth factors, additional components of the extracellular matrix, cytokines, hormones and drugs. In some embodiments, the extracellular matrix proteins can bind to these materials. These biologically active materials, if present, can be readily available to the cultured cells to moderate or regulate their properties or behavior.

The present invention provides a method of preparing a stable, ready-to-use cell-culturing system. This method includes applying an extracellular matrix coating composition to a cell culture surface coated with plasma polymerized film, wherein the total protein concentration in the coating composition is about 1 ng/mL to about 1 mg/mL. The method also includes immobilizing proteins in the coating composition on such film-coated vessel over a period of time; and removing the excess coating composition from the film-coated plates.

The coating composition is generally applied in the following quantities: approximately 0.5 to 2.0 mL of the coating composition may be applied to a well in a 6-well multiwell plate; about 0.25 to 1.0 mL may be applied to a well in a 12-well or 24-well multiwell plate; about 50 μL to 100 μL may be applied to a well in a 96-well plate; about 0.5 to 2.0 mL may be applied to a 35 mm dish; about 0.5 to 4.0 mL may be applied to a 60 mm dish; about—2.0 to 12.0 mL may be applied to a 100 mm dish; about 0.5 mL to 4.0 mL may be added to a T25 flask (having 25 $cm^2$ cell attachment surface); about 2.0 mL to 12.0 mL may be added to a T75 flask (having 75 $cm^2$ cell attachment surface); and, about 5.0 mL to 25.0 mL may be added to a T175 flask (having 175 $cm^2$ cell attachment surface).

After application, the coating composition is maintained on the film-coated surface to permit adsorption of the extracellular matrix proteins in the composition to the plasma polymerized plates. The coating composition may be maintained in an uncontrolled environment (e.g., room temperature) or a controlled environment (e.g., heated or chilled conditions). In particular, coated plasma polymerized plates are desirably incubated at temperatures from about 22° C. to about 37° C., and for a period of time of about 30 minutes to about 4 hours to permit adsorption of the proteins to the substrate surface. Alternatively, the coated plasma polymerized plates may be incubated at 4° C. overnight to 2 weeks prior to use. The excess coating composition is removed from the coated substrate immediately prior to use for cell culture to remove the unadsorbed proteins and remaining solution.

The cell culturing systems of the present invention can be used in various applications, including culturing of embryonic stem (ES) cells, mesenchymal and neuronal stem cells. In a preferred embodiment, a xeno-free, defined cell culture substrate may be useful for maintaining the self-renewal and pluripotency characteristics of undifferentiated ES and adult stem cells for extended periods of time.

In some embodiments, the ES cells, particularly human ES (hES) cells, may be cultured using a cell culturing vessel of the subject invention. For example, hES cells include, but are not limited to, the following cell lines: H1, H9, and H14, for example. These cell lines are available, for example, from WiCell Research Institute, Madison, Wis.

The cell culturing surface of the subject invention may be used to culture stem cells. The method may include culturing embryonic stem cells and providing a cell culturing system including a culture vessel with a plasma polymerized surface; and a coating thereon of a coating composition. The coating composition includes a mixture of extracellular matrix proteins and an aqueous solvent, the total protein concentration in the coating composition being about 1 ng/mL to about 1 mg/mL. The culturing method may also include adding a suspension of embryonic stem cells to the cell culturing system; and incubating the embryonic stem cells at 5% $CO_2$ in humidified air at 37° C. to produce undifferentiated colonies for embryonic stem cell expansion.

In further embodiments, a culture medium is utilized in the cell cultures. The culture medium may include base media and supplements to assist in the adherence of stem cells to the cell culturing substrate. In some embodiments, a culture medium such as mTeSR™1 (StemCell Technologies Inc.) may be included. It is noted, however, that the method of culturing is not limited to this culture medium.

In some embodiments, adult stem cells, which may be mesenchymal stem cells, may be cultured with the subject invention. For example, mesenchymal stem cells may include, but are not limited to, bone marrow derived cells such as Poietics® Human Mesenchymal Stem Cells. These cells are available, for example, from Lonza (Wakersville, Md.).

In further embodiments, the culture medium used to culture the mesenchymal stem cells is a serum free culture media such as STEMPRO® MSC SFM (Invitrogen Corporation, Carlsbad, Calif.). It is noted, however, that the method of culturing is not limited to this culture medium.

In other embodiments, neuronal stem cells, which may be hES cell derived, may be cultured with the subject invention.

In further embodiments, the culture medium used to culture the hES cell derived neuronal stem cells is a serum free culture media on DMEM/F12+Glutamax, N2, B27, bFGF and Pen/Strep.

The culture system of the present invention can be used to test various inhibitors or stimulators to determine their effectiveness in a cell study. Stimulators can include growth factors, which are known in the art. For example, these can include one or more of platelet derived growth factors (PDGF), e.g., PDGF AA, PDGF BB; insulin-like growth factors (IGF), e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-β1, TGF β1.2, TGF-β2, TGF-β3, TGF-β5; bone morphogenic proteins (BMP), e.g., BMP 1, BMP 2, BMP 3, BMP 4; vascular endothelial growth factors (VEGF), e.g., VEGF, placenta growth factor; epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M; nerve growth factor (NGF); stem cell factor; hepatocyte growth factor, and ciliary neurotrophic factor. Additional growth factors are described in Sporn and Roberts, *Peptide Growth Factors and Their Receptors I*, Springer-Verlag, New York (1990), which is hereby incorporated by reference. The term "growth factors" is intended to encompass presently unknown growth factors that may be discovered in the future, since their characterization as a growth factor will be readily determinable by persons skilled in the art.

In the embodiments of the present invention, the culture medium may be supplemented with serum, but is preferably serum-free. The culture medium may be a medium that is previously conditioned by exposure to fibroblast feeder layer cells (i.e. feeder conditioned medium). A suitable, defined serum-free medium, mTeSR™1, for culturing human embryonic stem cells is available from StemCell Technologies, Inc. A suitable, serum-free medium for culturing bone marrow derived mesenchymal stem cells, STEMPRO® MSC SFM, is available from Invitrogen Corporation (Carlsbad, Calif.).

Methods of Preparation

The present invention provides a method of preparing a stable, ready-to-use cell culturing substrate. This method includes applying an extracellular matrix coating solution to a plasma polymerized film-coated surface of a cell culture vessel, wherein the total protein concentration in the coating solution is about 1 ng/ml to about 1 mg/ml. The method also includes maintaining the coating solution on the film-coated surface so as to allow immobilizing of proteins from the coating solution on the substrate surface; and removing the excess coating solution from the substrate. In some aspects, one or more coating solutions may be added to the plasma polymerized film-coated surface.

In some embodiments coating solutions, with the same or different ECM proteins, may be serially applied. An optional washing step may be utilized between coating applications. In some embodiments, the washing step(s) may include washing the substrate with distilled water, a buffer (e.g., PBS) or a culture medium. In other embodiments, the washing step(s) may include washing the substrate with a blocking solution.

The coating solution, including the extracellular matrix components, can be maintained on at least one surface of a film-coated cell culturing surface, such as the surface of a cell culturing vessel (e.g., flask or cell culture plate), at a temperature and/or time period sufficient to allow adsorption of the extracellular matrix proteins to the coated surface. For example, the film-coated cell culturing vessel can be maintained at room temperature from about 1 to about 4 hours to allow adsorption. Alternatively, the container can be incubated at 4° C. over a period of time (e.g. 4 hours to 2 weeks). Also, coated substrates may be incubated at temperatures from about 22° C. to about 37° C., and for a period of time of about 30 minutes to about 4 hours to permit adsorption of the proteins to the substrate surface. Any excess coating solution is thereafter removed (e.g., by aspiration), and the coated substrate may be washed with an aqueous solvent (e.g., water, buffer, $ddH_2O$, culture media) to remove unbound proteins. Use of a blocking solution, as described above, increases the stability of the coated substrate.

After the coating is applied, it can optionally be sterilized. In one embodiment, the apparatus is sterilized using ultraviolet (UV) light.

In some aspects, the cell culturing substrate may be frozen immediately after the coating solution is applied to the film-coated surface. The frozen cell culturing substrate may be stored at −20° C. for up to 3 months and then thawed prior to use. For example, laminin as the ECM protein may be applied as a coating solution, as described above, with the resulting cell culturing surface being frozen and stored.

The following examples are for illustrative purposes and are not intended to, in any way to limit the embodiments and uses of the present invention.

EXAMPLES

Example 1

ECM Coating on Chemically Defined Plasma Polymerized Surfaces

Chemically defined plasma polymerized culture vessels (12 or 6 multiwell plate format) were coated with various extracellular matrix (ECM) proteins. Individual or combined ECM proteins, diluted in Dulbecco's phosphate buffered saline (DPBS) or DMEM/F12 media, were added (1 mL/well for 6 well plates and 0.5 mL/well for 12 or 24 well plates) and the plates were coated for 2 hours at room temperature or at 37° C. Coating solution was removed immediately prior to use for hES cell culture experiments. The following ECMs were used in the experiment: ECMs include but are not limited to human fibronectin, human laminin, human vitronectin, human collagen IV, BD Matrigel™ hESC-qualified Matrix, ProNectin® F Plus; a fibronectin-like engineered protein polymer from Sigma; Retronectin another recombinant fragment of human fibronectin from Takara Bio USA.

Plasma polymerized 6 well plates (BD Primex 1 (which includes amines and a positively charged surface, Cat #359296) and BD Primex 2 (which includes carboxyls and a negatively charged surface, Cat #359297)), that are chemically defined, were coated with various animal free ECMs. Plasma polymerized 24 well plates (BD PureCoat amine, a positively charged plasma polymerized surface, Cat #354723 or 356723), that are chemically defined, were coated with various human and animal derived ECMs.

The coating solution was made by diluting single or a mixture of ECM proteins in Dulbecco's phosphate buffered saline at a final protein concentration of 5 µg/mL to 50 µg/mL.

The coating solution was added at a volume of 1 mL per well for a 6 well plate or 0.5 mL per well for a 12 well plate.

The coating solution was incubated on plasma polymerized plates for a minimum of 2 hours at room temperature or overnight at 4° C.

The coating solution was removed immediately prior to use of the plates for hES cell culturing experiments.

Example 2

Culture of Human Embryonic Stem Cells on ECM Coated Plasma Polymerized Surfaces hES Cell Culture on ECM-Coated Plasma Polymerized Surface hES cells (H1, H9 or H14 lines from WiCell Institute) were initially plated onto plasma polymerized plates (with or without ECM coating) from positive control plates (i.e. hESC cells grown on 6 well TC plates coated with BD Matrigel™ hESC-qualified Matrix and grown in mTeSR™1 medium).

Cells on positive control plates were treated with dispase (2 mg/mL) for 5 minutes at 37° C., followed by four quick washes with DMEM/F12 medium and then mechanically dissected to small clumps in a small volume of mTeSR™1 medium using plastic pipettes or pipette tips. Clumps of hES cells resuspended in mTeSR™1 medium were seeded onto test surfaces at a 1:3 to 1:6 split ratio and cultured in an incubator at 5% $CO_2$ in humidified air at 37° C. Culture medium was replaced daily and cells were typically dissociated every 4 to 6 days after initial plating.

hESC Dissociation on Plasma Polymerized BD Primex 1 Plates hES cells cultured on BD Primex 1 plates coated with BD human fibronectin were routine dissociated with TryPLE select (Invitrogen, diluted 1:2 (v:v) with DMEM/F12) for sub-culturing and long-term maintenance. Briefly, spent culture medium was removed, cells were rinsed once with DMEM/F12 medium, and treated with diluted TryPLE select (1 mL/well) for 2 minutes at room temperature. Dissociation reagent was then promptly removed and cells were washed three times in rapid succession with DMEM/F12 medium. mTeSR™1 medium (StemCell Technologies, Inc.) was then added to the treated cells and colonies were mechanically dissected to small clumps using a 5 mL plastic pipette or pipette tips. Dissociation and plating of cells were then carried out as described in the above section.

hES Cell Colony Attachment Assay

Figure 1B:
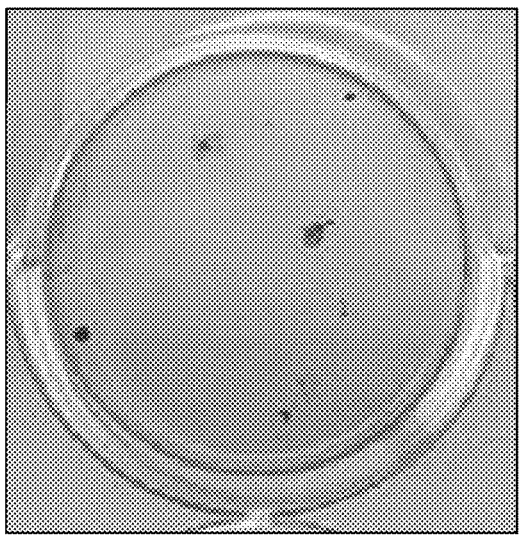
Figure 1C:
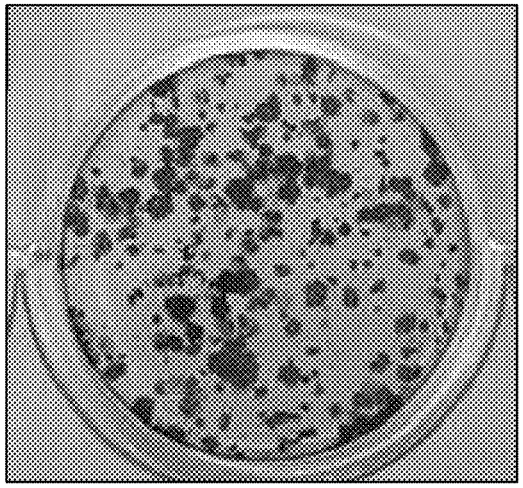

Attachment of hES cells on plasma polymerized surfaces coated with various ECM proteins were compared.

hES cells were fixed for 20 minutes with 4% paraformaldehyde at room temperature followed by two washes with Dulbecco's phosphate buffered saline (DBPS) for 5 minutes each. Cells were then stained for 5 minutes with crystal violet stain (diluted 1:10 with DPBS) and washed once with DPBS. The plates containing fixed and crystal violet stained cells were scanned using a laser scanner and the attached colonies per well were visualized (FIG. 1). FIG. 1A is (TC)-treated polystyrene plates coated with BD Matrigel™ hESC-qualified matrix, FIG. 1B is TC plates coated with BD human fibronectin; and FIG. 1C BD Primex 1 plates (Cat #359296) coated with BD human fibronectin and cultured with mTeSR™1 medium (StemCell Technologies, Inc.).

Colony attachment and morphology of the cells were also routinely monitored using a phase contrast microscope. As evidenced by FIG. 2A and FIG. 2B, hES cells (H9 line) were grown on plasma polymerized BD Primex 1 plates (Cat #359296) coated with BD human fibronectin for 18 passages (FIG. 2B). Cell morphology on the BD Primex 1 plates coated with fibronectin was very similar to hES cell colonies grown on positive control substrate, TC plates coated with BD Matrigel™ hESC-qualified matrix (FIG. 2A). hES cells maintained a predominantly undifferentiated state when cultured on both of these substrates.

Results

Human embryonic stem (hES) cells (H9 line) were seeded on tissue culture (TC)-treated polystyrene plates coated with BD Matrigel™ hESC-qualified matrix or human fibronectin; and on BD Primex 1 coated with human fibronectin. Cells were and cultured with mTeSR™1 medium (StemCell Technologies, Inc) for four days, fixed and stained with crystal violet. Relative cell attachment on each surface is shown in FIG. 1. As can be seen colony attachment on BD Primex 1 coated with human fibronectin (FIG. 1C) is comparable to positive control substrate (TC plates coated with BD Matrigel™ hESC-qualified matrix, FIG. 1A). However, TC surface coated with human fibronectin did not support appreciable hES cell colony attachment or growth with mTeSR™1 medium (FIG. 1B).

Results of hES cell colony attachment is shown below on BD Primex 1 and TC plates with or without various types of human fibronectin protein coating:

TABLE 1

|  | BD Primex 1 | TC |
|---|---|---|
| Uncoated | 0 | 0 |
| BD Matrigel ™ hESC-qualified Matrix | 3 | 3 |
| BD fibronectin (from human plasma) | 3 | 1 |
| Sigma fibronectin (from human plasma) | 3 | Not tested |
| Sigma fibronectin (from human Foreskin Fibroblast) | 2 | Not tested |
| Retronectin (recombinant Fragment of humanfibronectin from Takara Bio USA) | 3 | Not tested |
| Pronectin ® F Plus (humanfibronectin-like engineered protein polymer, Sigma) | 1 | Not tested |

COLONY ATTACHMENT SCALE
0: no colony attached
1: low (~1 to 10 colonies)
2: moderate (~10-20 colonies)
3: high (typically >20 colonies and comparable to positive control
Positive control = TC surface coated with pre-qualified BD Matrigel ™

Surface was considered comparable to positive control based on approximate number of colony attachment, cellular morphology within the colonies (i.e. compact vs. single cells), rate of proliferation and degree of spontaneous differentiation.

Results of hES cell colony attachment is shown below on plasma polymerized BD Primex 1 and BD Primex 2 plates with or without various ECM protein coating:

TABLE 2

|  | Plasma polymerized surface | |
|---|---|---|
|  | BD Primex 2 | BD Primex 1 |
| Uncoated surface | 0 | 0 |
| Sigma human Laminin | 3 | 2 |
| BD human fibronectin | 2 | 3 |
| BD human fibronectin + BD human collagen IV | Not tested | 2 |
| BD human fibronectin + human vitronectin | Not tested | 3 |
| BD Human Matrix | 1 | 1 |

COLONY ATTACHMENT SCALE
0: No colony attached
1: low (~1 to 10 colonies)
2: moderate (~10-20 colonies)
3: high (typically >20 colonies)

Surface was considered comparable to positive control based on approximate number of colony attachment, cellular morphology within the colonies (i.e. compact vs. single cells), rate of proliferation and degree of spontaneous differentiation.

Example 3

Characterization of Undifferentiated hESCs

Figure 2A:
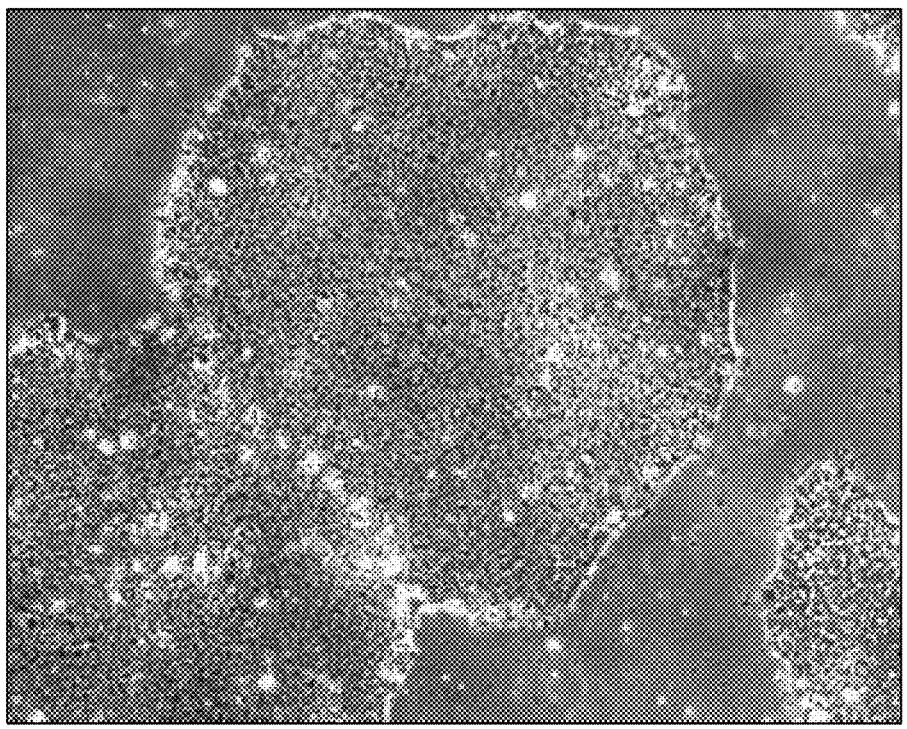
FIG. 2 comparison of typical hES cell colony morphology on selected substrates: TC plates coated with an extracellular matrix, (such as, Matrigel™) (FIG. 2A) and plasma polymerized plates coated with human fibronectin for 18 passages (FIG. 2B).
Figure 2B:
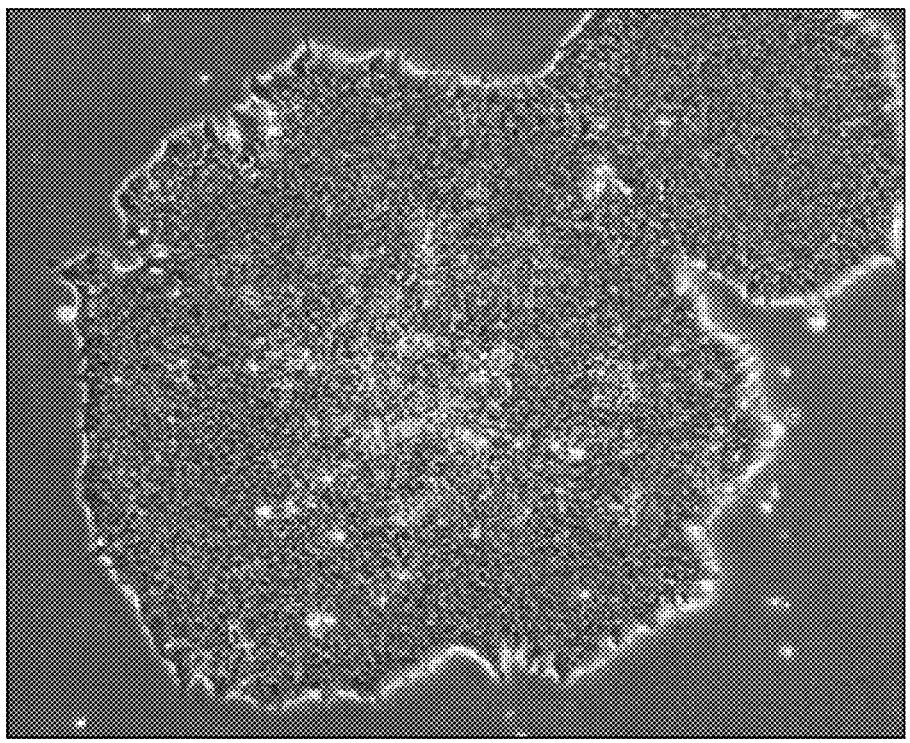

Morphological analysis (FIG. 2) reveals that hES cells maintained a predominantly undifferentiated state when cultured with mTeSR™1 on BD Primex 1 plates (Cat #359296) coated with BD human Fibronectin (FIG. 2B) and was comparable to those cultured on positive control substrate (TC plates coated with BD Matrigel™ hESC-qualified matrix, FIG. 2A).

Figure 3A:
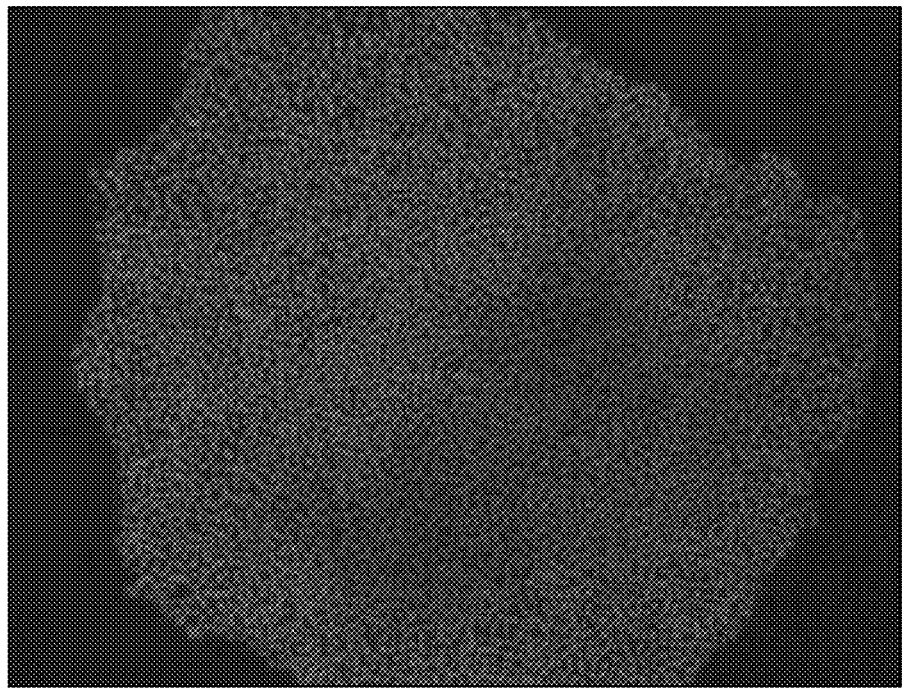
FIG. 3 Immunocytochemistry staining of undifferentiated hES cells (H9 line) expressing OCT-3/4 marker protein expressed in their nuclei. Cells were cultured with growth media on plasma polymerized plates coated with human fibronectin (FIG. 3B) and on TC plates coated with an extracellular matrix (such as, Matrigel™) (positive control, FIG. 3A).
Figure 3B:
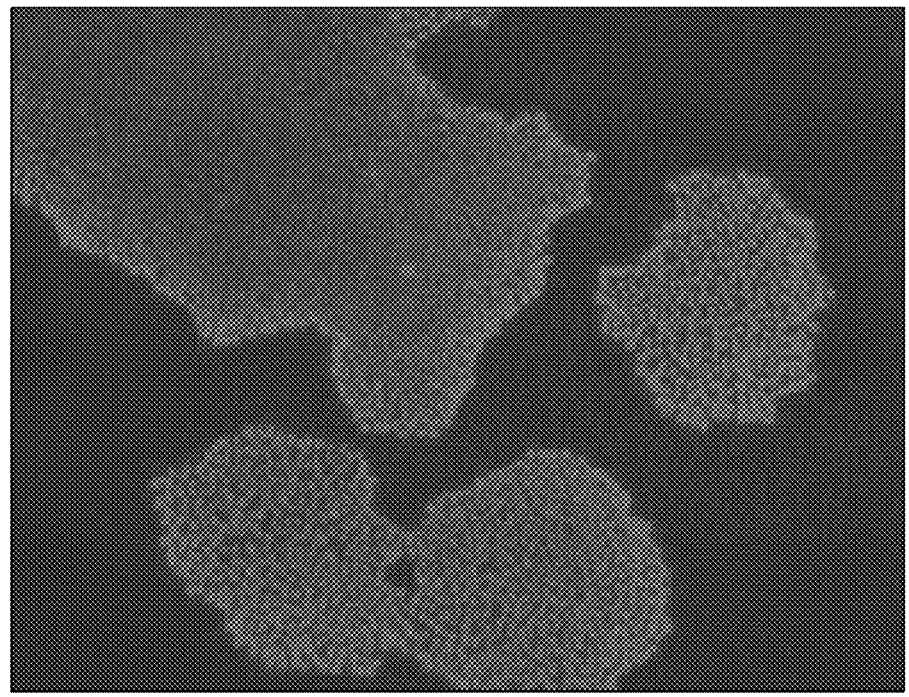
Figure 4:
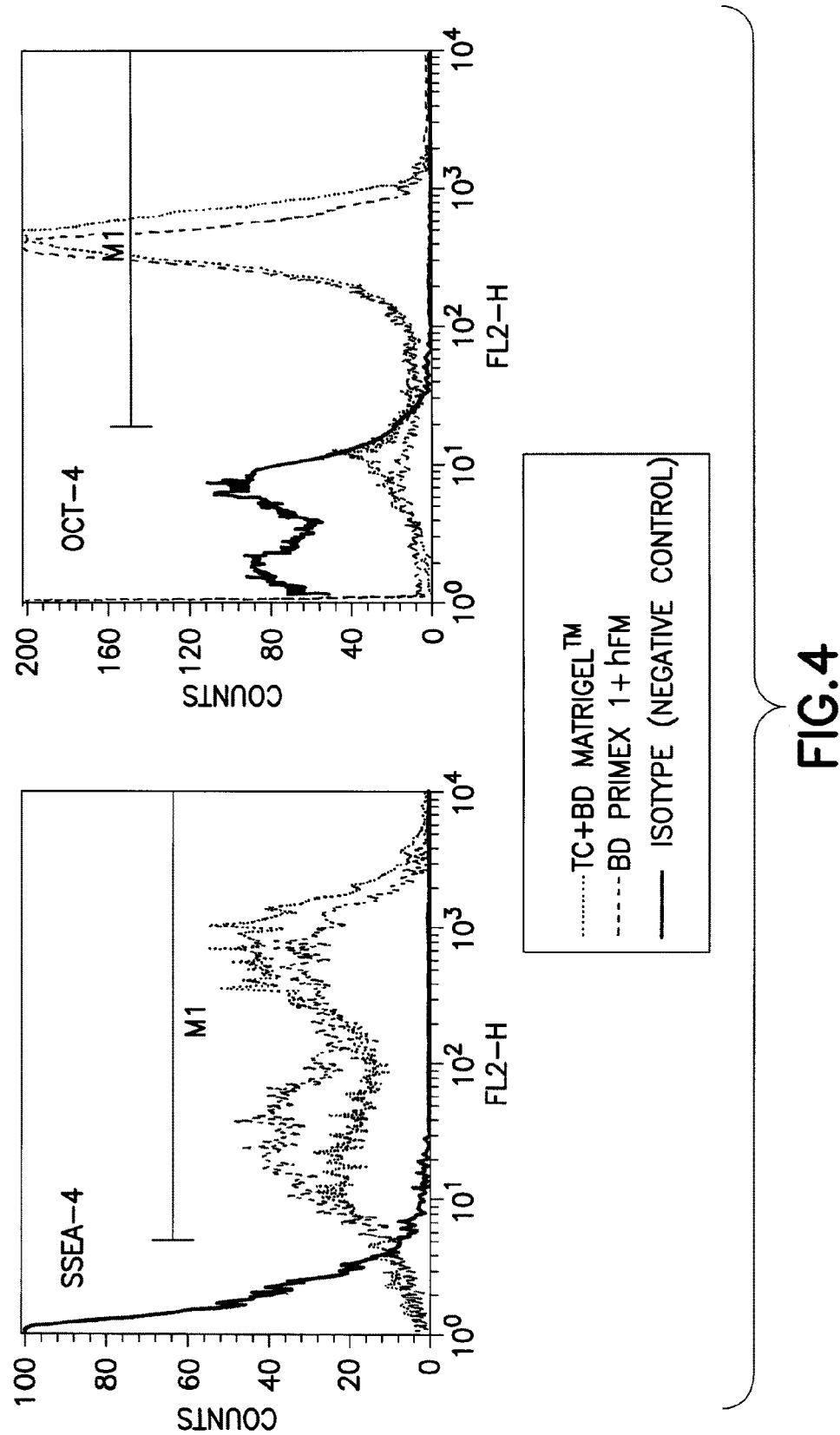
FIG. 4 Quantitative Fluorescence Activated Cell Sorter (FACS) analysis of undifferentiated hES cell specific marker protein expression of cells grown on plasma polymerized plates coated with human fibronectin and on TC plates coated with an extracellular matrix (such as, Matrigel™) (positive control).

Expression of the undifferentiated marker OCT-3/4 was comparable for cells cultured with mTeSR™1 on BD Primex 1 plates coated with BD human fibronectin (FIG. 3B) and on positive control substrate (TC plates coated with BD Matrigel™ hESC-qualified matrix, FIG. 3A).

Quantitative FACS analysis (protocol outlined below in Example 5) revealed that expression of undifferentiated hES cell-specific marker expression (OCT-3/4 and SSEA-4) for hES cells (H9 line) cultured on BD Primex 1 coated with BD human fibronectin for sixteen passages were comparable to positive control cells (cultured on TC coated with BD Matrigel™ hESC-qualified matrix). The relative percentage of cells that expressed undifferentiated markers are summarized in Table 3 below.

TABLE 3

|  | Cells positive for undifferentiated markers (%) | |
|---|---|---|
| Surface | OCT-4 | SSEA-4 |
| BD Primex 1 | 86.82 | 95.58 |
| TC + BD Matrigel ™ | 87.2 | 90.95 |

Example 4

Inducing Spontaneous Differentiation by Embryoid Body Formation hESC colonies were dissociated with either TryPLE select (Invitrogen) in the same manner as described above in Example 2.

Dissociated cell clumps were plated on petri dishes (not tissue culture treated) or low attachment 6 well plates in differentiation medium (DMEM/F12 medium supplemented with 20% fetal bovine serum (FBS), 10 mM non-essential amino acids, 1 mM L-glutamine, 0.1 mM beta-mercaptoethanol).

Cell clumps cultured in differentiation medium formed embryoid bodies (EBs) in suspension and were grown for 4-15 days. Subsequently the EBs were either analyzed by QRT-PCR (protocol known in prior art) for germ layer marker gene expression; or re-plated on gelatin-coated TC plates, further differentiated in DMEM supplemented with 20% FBS for additional periods of time, and analyzed using immunohistochemistry for presence of germlayer specific protein expression.

Example 5

Characterization of Pluripotency of hESCs

Figure 5:
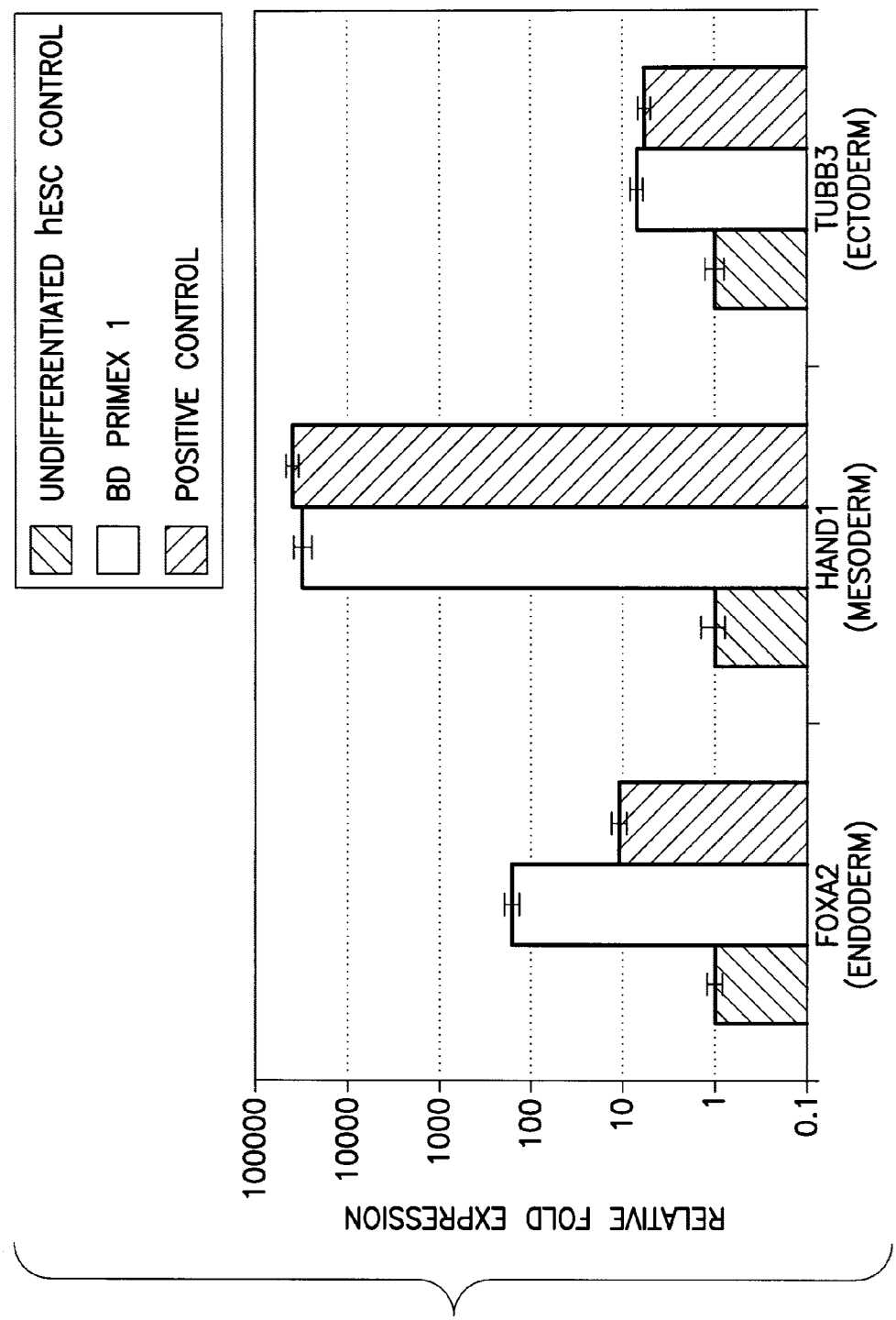
FIG. 5 Quantitative real time-polymerase chain reaction (QRT-PCR) analysis of germline-specific marker gene expression in embryoid bodies generated from hES cells cultured on plama polymerized plates coated with human fibronectin and on TC plates coated with an extracellular matrix (such as, Matrigel™) (positive control).
Figure 6A:
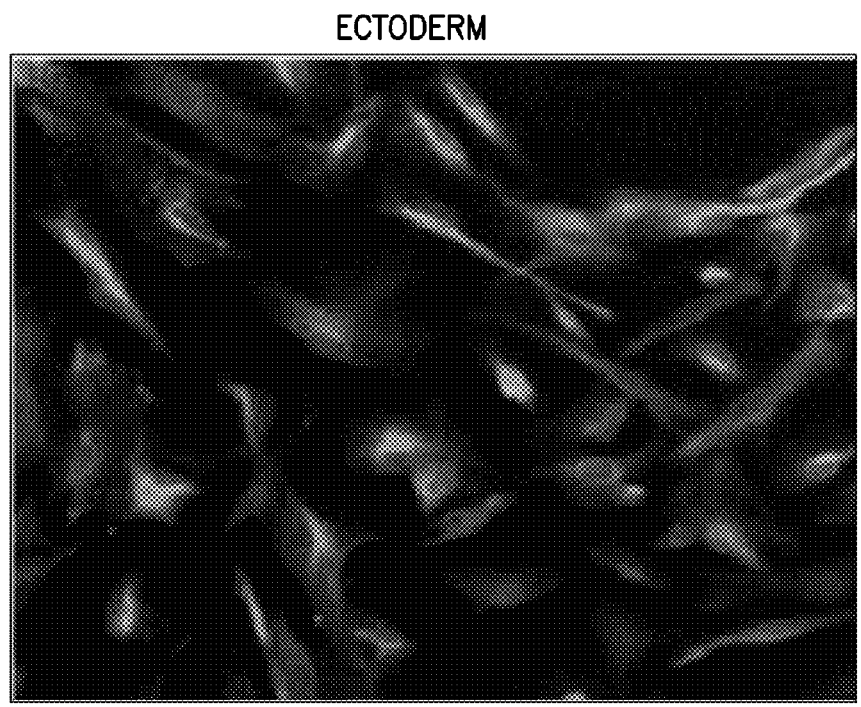
FIG. 6 Immunocytochemistry analysis of germline-specific marker protein expression in hES cell-derived differentiated cells.
Figure 6B:
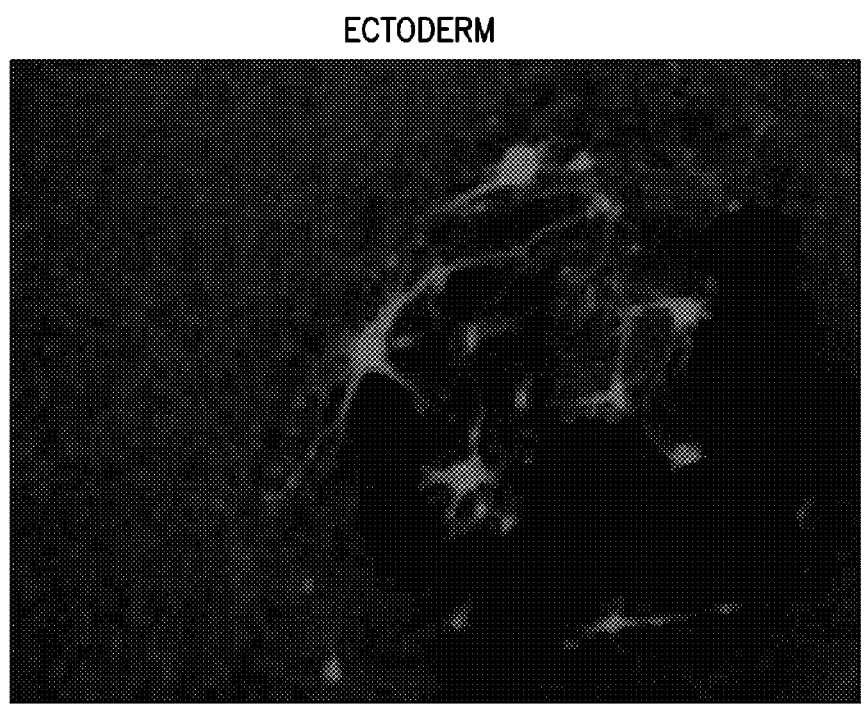
Figure 6C:
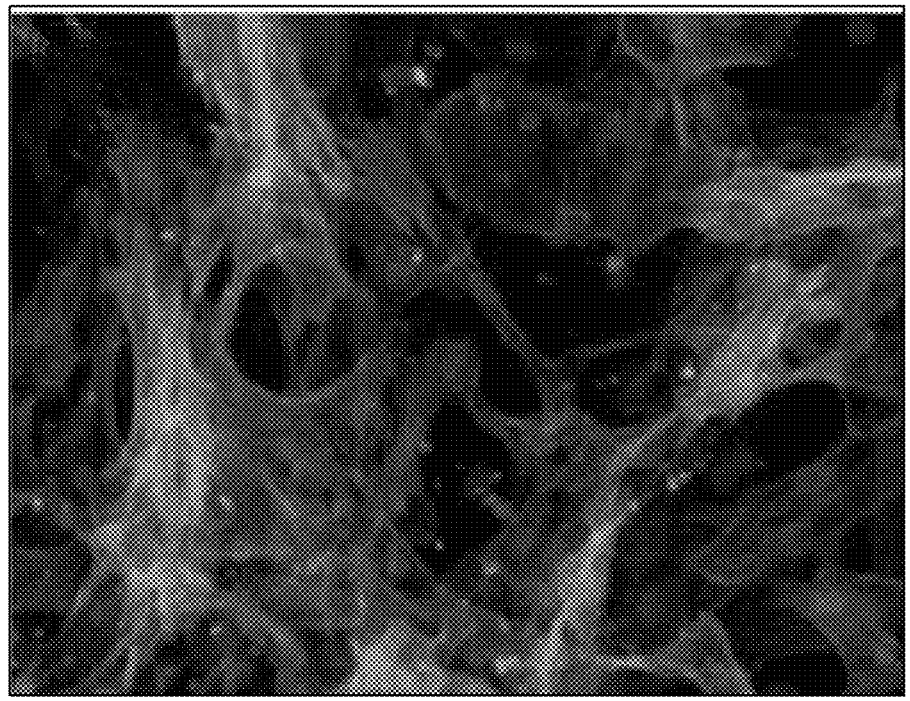
Figure 6D:
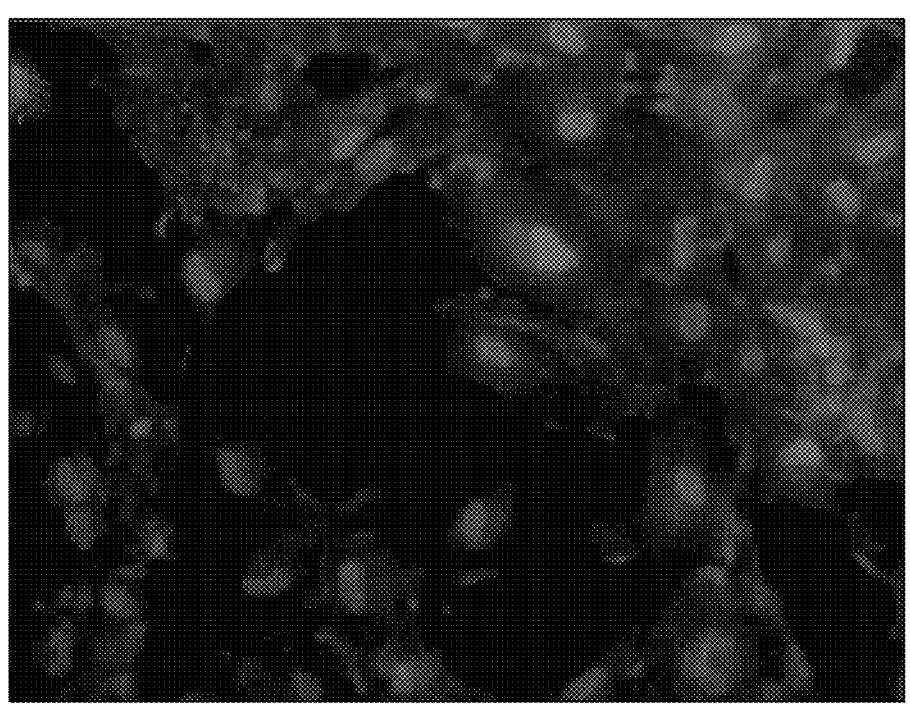

H9 hES cells (following culture for 13 passages on BD Primex 1 plates coated with BD human fibronectin) were differentiated into embryoid bodies (EBs). Expression of 3 germ layer markers in EBs was determined by QRT-PCR (FIG. 5). All three germ layer markers FoxA2 (forkhead box A2 expressed in Endoderm), HAND1 (heart and neural crest derivatives expressed 1 in Mesoderm) and tubulin TUBB3 (tubulin beta 3 in Ectoderm) were detected. Cells grown on TC plates coated with BD Matrigel™ hESC-qualified Matrix represents positive control. Expression of the germ layer markers relative to undifferentiated cells cultured on BD Primex 1 plates coated with BD human fibronectin (control) is also shown. As can be seen, there is a significant increase in expression of all 3 germ layer markers for EBs generated from cells cultured on BD Primex 1 plates coated with BD human fibronectin and expression is comparable to positive control. The above data suggest that the cells cultured on Primex 1 with fibronectin coating maintain their pluripotency.

Germ layer marker protein expression after spontaneous differentiation following EB formation is shown in FIG. 6. hES cells (H9 line) were cultured on BD Primex 1 plates coated with BD human fibronectin for 3 passages. Cells were differentiated into EBs for 10 days and transferred to gelatin-coated TC plates and cultured for 10 additional days in DMEM medium supplemented with 20% FBS. Expression of germ layer markers was determined by immunohistochemistry.

Example 6

Immunocytochemistry Protocols

The present example is directed to an immunocytochemistry protocol used to test for marker expression of undifferentiated hES cells (data outlined in Example 3 and shown in FIG. 3). The present protocol is for cells grown on 6-well plates. The same protocol was also used for detecting expression of germ layer specific proteins in differentiated hES cells (data outlined in example 4 and shown in FIG. 6). For the latter study, cells were grown on 12-well plates and half of the volumes indicated in the following protocol were used per well.

Cultured hES cells were washed with 2 mL of Dulbecco's phosphate buffered saline (DPBS). Then, the cells were fixed with 1 mL of 4% paraformaldehyde for 20 minutes at room temperature. The fixed cells were washed twice with 2 mL of DPBS for 5 minutes each. Subsequently, the cells were blocked with 1 mL of 0.1% bovine serum albumin (BSA) and 10% normal goat serum in DPBS. During the blocking step, the primary antibody working solution was prepared with DPBS containing 1% BSA and 10% normal goat serum to a final desired antibody concentration. It is noted, that for both the blocking solution, and the primary antibody solution, the normal serum may be replaced with that from another species depending on the host species of the secondary antibody.

After blocking, the cells were incubated with 1 mL/well of the diluted antibody working solution for 2 hours at room temperature or overnight at 2-8° C. Then, the cells were washed three times with 2 mL of DPBS containing 1% BSA for 5 minutes each wash.

The secondary antibody was diluted 1:2000 in DPBS containing 1% BSA. Useful fluorescent secondary antibodies included Alex 488 or 594-conjugated appropriate secondary antibodies (Invitrogen-Molecular Probes). The cells were incubated with the diluted secondary antibody 1 mL/well for 60 minutes at room temperature in the dark. Subsequently, the cells were washed three times with 2 mL of DPBS containing 1% BSA for 5 minutes each wash. The cells were thereafter covered with 2 mL of DPBS and visualized and imaged with a fluorescent microscope.

Example 7

FACS Analysis Protocol

Confluent cultures of human embryonic stem (hES) cells (H9 line) grown on 6 well plates were briefly rinsed with Dulbecco's phosphate buffered saline (DPBS) and treated with 1 mL/well 0.25% Trypsin/EDTA (Invitrogen) for 2-3 minutes at 37° C. to dissociate the cells from the surface. Trypsin was inactivated by adding 2 mls/well DMEM/F12 medium containing 20% fetal bovine serum (FBS). Cells were then gently triturated by pipetting up and down, and pelleted by centrifugation at 1000 rpm for 5 minutes.

For intracellular antigens (e.g. OCT-3/4), the cell pellet was resuspended and fixed in 1% paraformaldehyde (1 mL/tube) for 10 mins at 37° C. Fixed cells were washed one briefly with 3 mL/well perm/wash buffer (BD Pharmingen). Cells were pelleted by centrifugation, the supernant was discarded and the cell pellet was resuspended in 3 mL/well perm/wash buffer and incubated on ice for 15 minutes to permeabilize the cells. Following permeabilization, cells were pelleted once more by centrifugation and resuspended in 100 µl of perm/wash buffer and probed with appropriate primary antibodies (~$3\times10^5$ cells incubated with 500 ng of primary antibody). Following 1 hour of incubation, cells were washed with 3 mL of perm/wash buffer and resuspended in 100 µL of the same buffer. Secondary antibody was added and cells were incubated for 30 minutes in the dark at room temperature. Following incubations, cells were washed as above and resuspended in 200 µL of perm/wash buffer containing 1 µg/ml of propidium iodide (Sigma) to identify viable cells. Fluorescence-activated cell sorter (FACS) analysis was performed by using a FACS Calibur Flow Cytometer (BD). A total of 30,000 events were analyzed per sample and data was analyzed using CellQuest 3.0 software (BD).

For surface antigens (such as SSEA-4, TRA-1-60, TRA-1-81 etc.) a similar protocol was followed with some exceptions. Following dissociation, cells were resuspended in 0.5 mL of DPBS containing 25% FBS. The fixation step was omitted for detection of surface antigens. All primary antibody incubations were carried out in DPBS containing 25% FBS on ice using 200 ng antibody per reaction, while secondary antibody incubation was carried out in the same buffer for 30 minutes in the dark at room temperature. All other steps were similar to the protocol outlined for intracellular antigens above.

Example 8

Fibronectin ELISA Assay

The performance of the ECM-coated BD Primex plates was further defined by the results of an ELISA assay for human fibronectin. For example, a fibronectin ELISA or laminin ELISA may be used to assess the amount of the ECM protein adsorbed on the substrate surface. By way of example, a human fibronectin ELISA assay, which was used to assess performance of the coated vessels is set forth below. A graph of fibronectin ELISA data for BD Primex 1 plates and TC plates coated with varying concentrations of human fibronectin is shown in FIG. 7.

In order to prepare a working primary antibody solution for the ELISA, 0.5 ml of a 1:100 (v/v) stock solution of rabbit anti-human fibronectin (Sigma; catalog no. F3648) was added to 40 ml of 0.5% bovine serum albumin (BSA) in Dulbecco's phosphate buffered saline (DPBS). In order to prepare a working solution of secondary antibody for the ELISA, 0.4 ml of a 1:100 (v/v) stock solution of goat anti-rabbit IgG-HRP (BD Pharmingen; catalog no. 554021) was added to 40 ml of 0.5% BSA in DPBS. The ELISA was performed using: ECM-coated 6-well BD Primex 1 plates prepared according to the present invention (test plates), TC plates coated with BD Matrigel™ hESC-qualified Matrix (positive control) or Falcon 6-well uncoated plates (catalog no. 353046; negative control). The plates were first washed 3 times with 2 mL/well wash buffer (DPBS with 0.02% Tween- 20). Then, 1 mL of 0.5% BSA in DPBS was added as a blocking solution, and the plates were incubated at room temperature for 1 hour. The BSA solution was then removed, and the plates were washed with wash buffer as described above. Next, 1 mL/well of the primary antibody working solution was added, and the plates were incubated for 2 hours at room temperature. After removing the primary antibody solution, the plates were again washed as described above. Subsequently, 1 mL/well of the secondary antibody working solution was added, and the plates were incubated at room temperature for 1 hour. After removing the secondary antibody solution, the plates were again washed as described above. Next, 1 ml/well of horseradish peroxidase (HRP) substrate, TMB (KPL; catalog no. 53-00-02) was added, and blue color was allowed to develop for 8 minutes. Subsequently, 1 mL of stop solution (KPL; catalog no. 50-85-05) was added, and the plates were swirled gently in order to facilitate mixing. Then, a 200 µl aliquot from each well of the 6-well plate was transferred to wells of a 96-well plate, and the absorbance was measured at 450 nm at room temperature using a spectrophotometer (SpectraMax® Plus384, Molecular Devices). The plates were read within 5 minutes after the stop solution was added. The mean absorbance per well was calculated for the test plates and positive control TC plates.

Figure 7A:
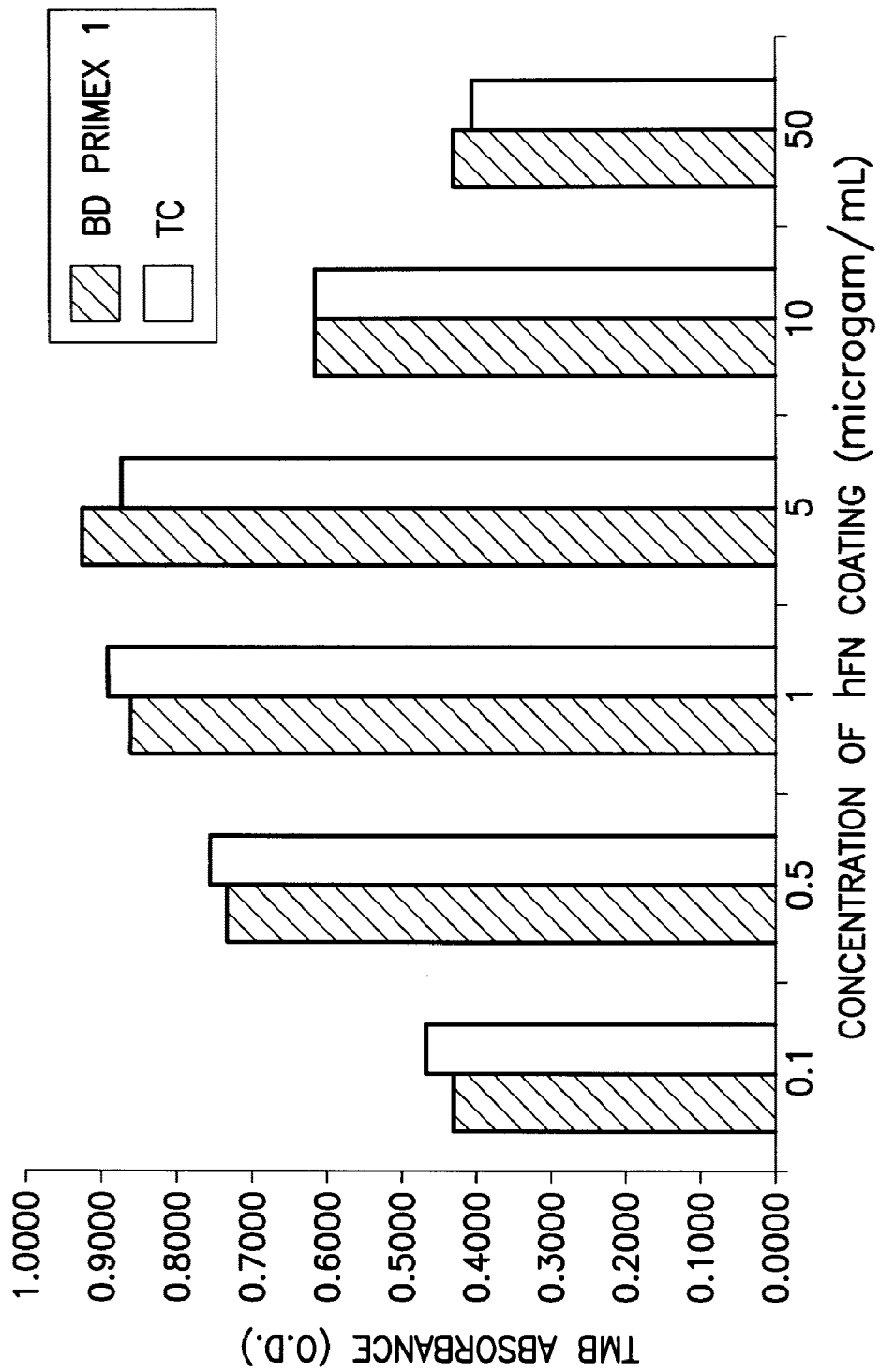
FIG. 7A Comparison of bound fibronectin on plasma polymerized plates and TC plates coated with different concentrations of human fibronectin and detected by anti-human fibronectin ELISA.

Results of Fibronectin ELISA Assay:

No significant difference in the amount of fibronectin attachment was detected between plasma polymerized BD Primex 1 plates as compared to TC plates (FIG. 7A). However, hES cell attachment and growth is supported on BD Primex 1 coated with BD human fibronectin (FIGS. 1C and 7B), and is not optimal on TC surface coated with BD human fibronectin (FIG. 1B). Hence there is no obvious correlation between concentration of fibronectin as detected by ELISA data and hES cell attachment and growth on BD Primex 1 plates.

Figure 7B:
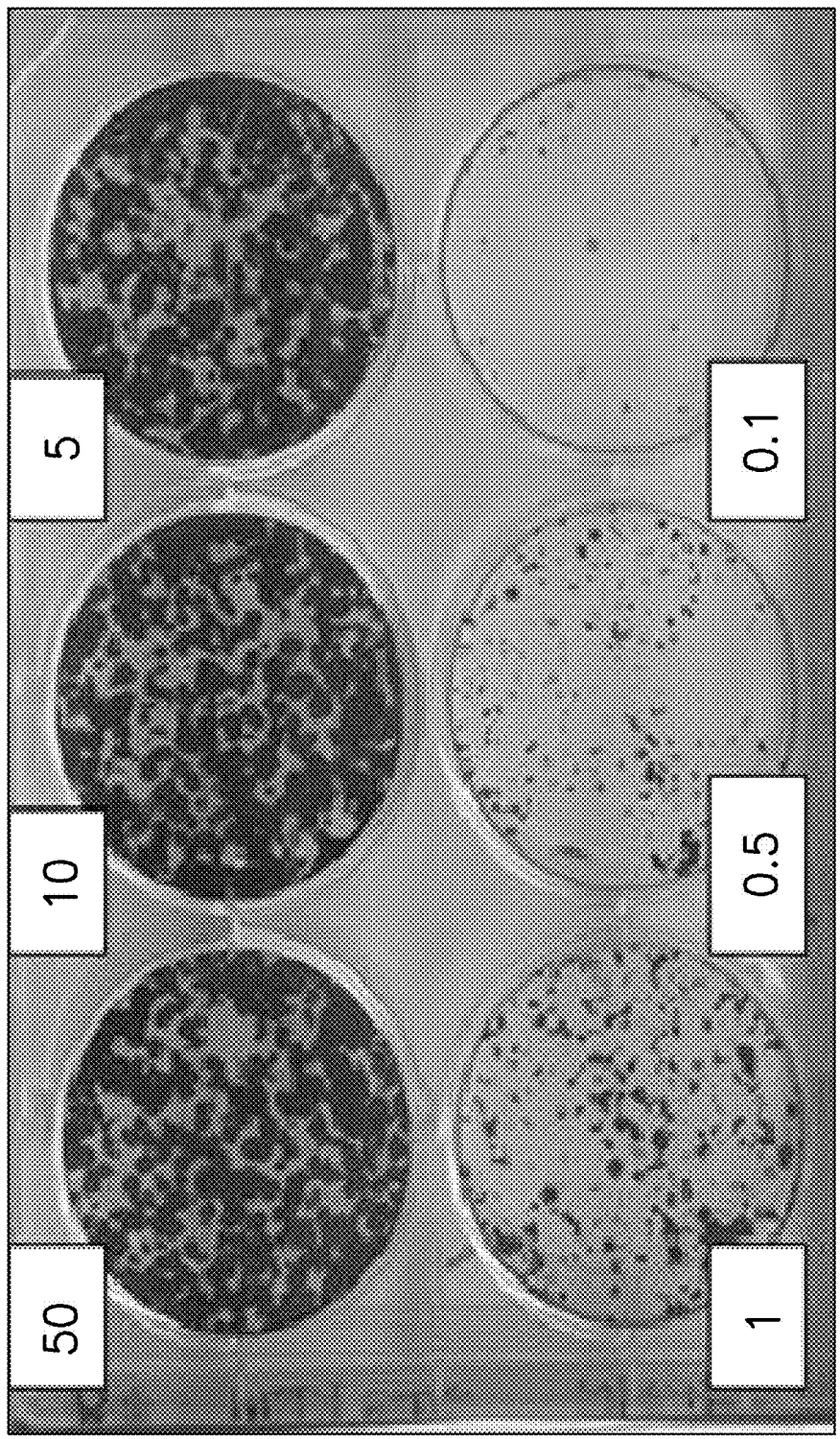
FIG. 7B Crystal violet staining of hES cells (H9 line) grown for 3 days on human fibronectin-coated plasma polymerized plates.
Figure 8A:
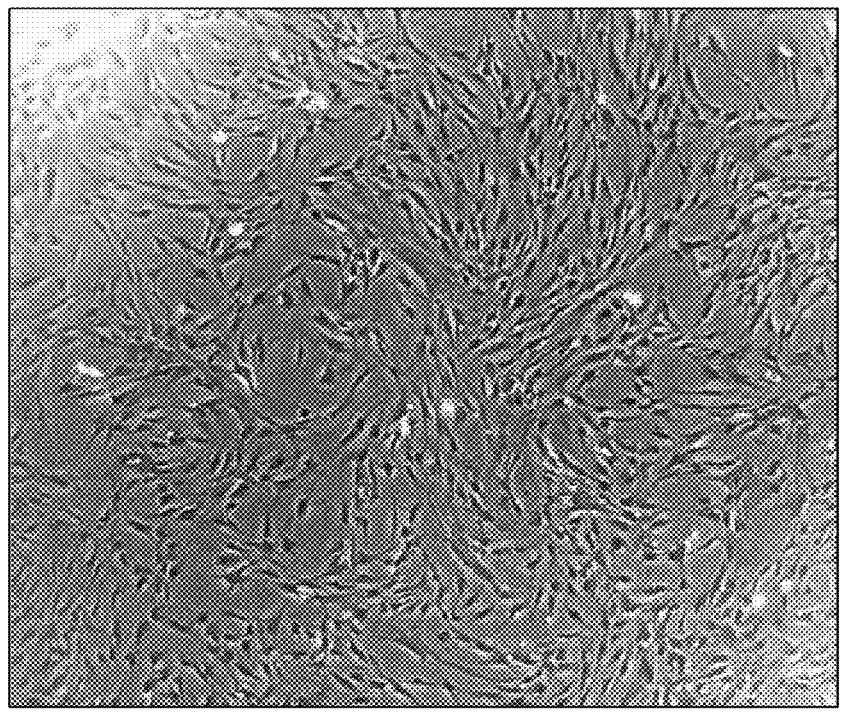
FIG. 8 Comparison of attachment and growth of human mesenchymal stem cells (MSC) on tissue culture plates in MSC media containing serum (FIG. 8A); and on plasma polymerized plates coated with human fibronectin and cultured in serum free MSC media (FIG. 8B).
Figure 8B:
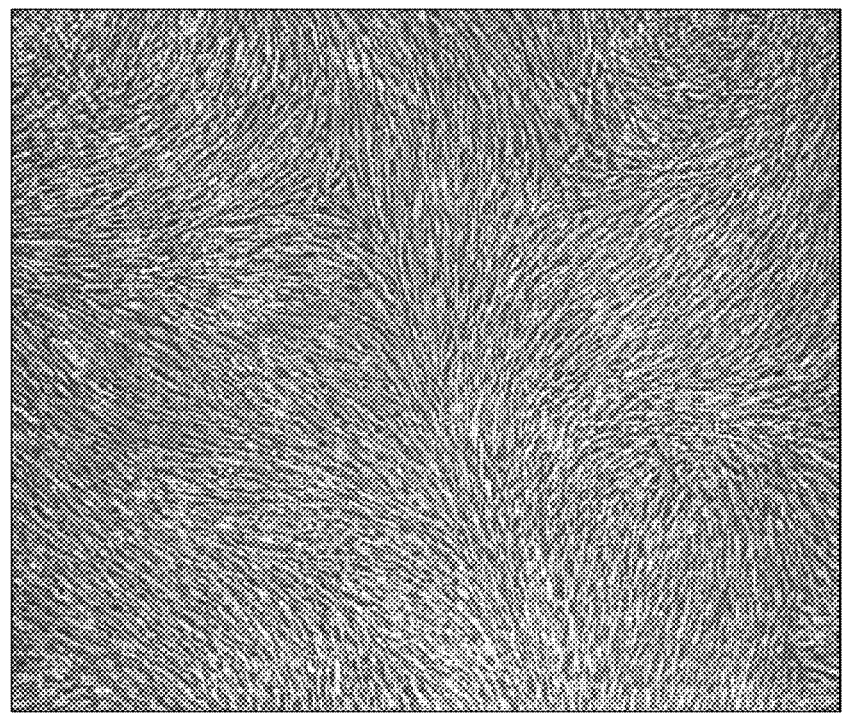

Human fibronectin concentration of 5 to 50 µg/mL supports good attachment and growth of hES cells on Primex 1 (FIG. 7B). However, close inspection of colony morphology suggests that 10-50 µg/mL is the best range for long-term culture of these cells.

Collectively this data suggest that it is not the amount of bound fibronectin, but rather the conformation of this ECM protein, that offers an advantage on plasma polymerized BD Primex 1 plates for hES cell attachment and growth.

Example 9

Figure 9A:
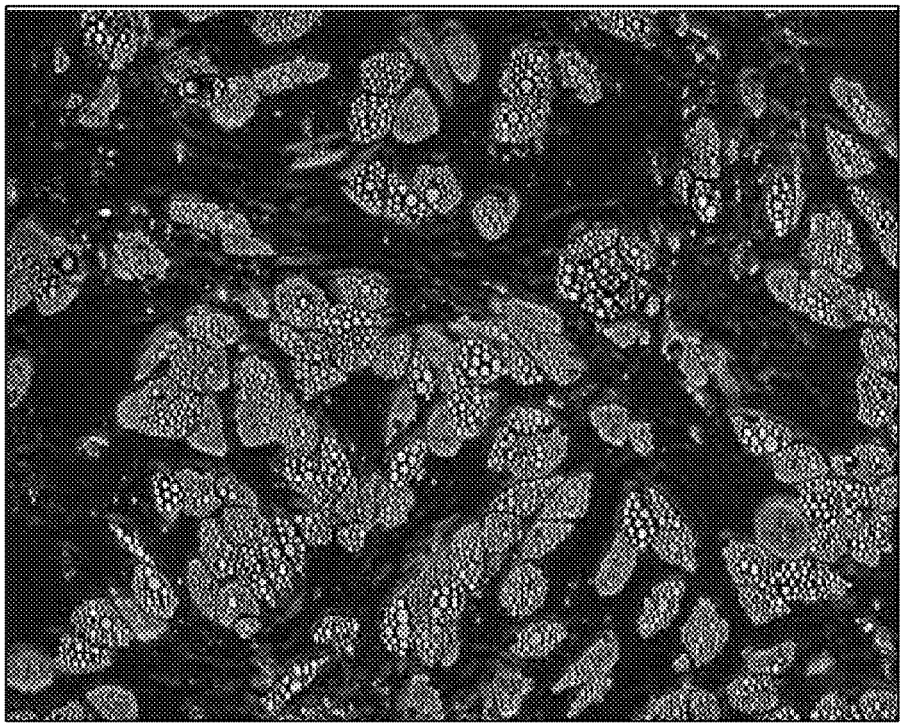
FIG. 9 Comparison of differentiation potential of human mesenchymal stem cells (MSCs) to adipocytes. MSCs at passage 5 were seeded on either uncoated tissue culture plates (FIG. 9A) or plasma polymerized plates coated with human fibronectin (FIG. 9B) and induced with adipogenic media. Cells plated on tissue culture plates were previously cultured with serum containing media. Cells plated on plasma polymerized plates coated with fibronectin were previously cultured on the same surface with serum free MSC media.
Figure 9B:
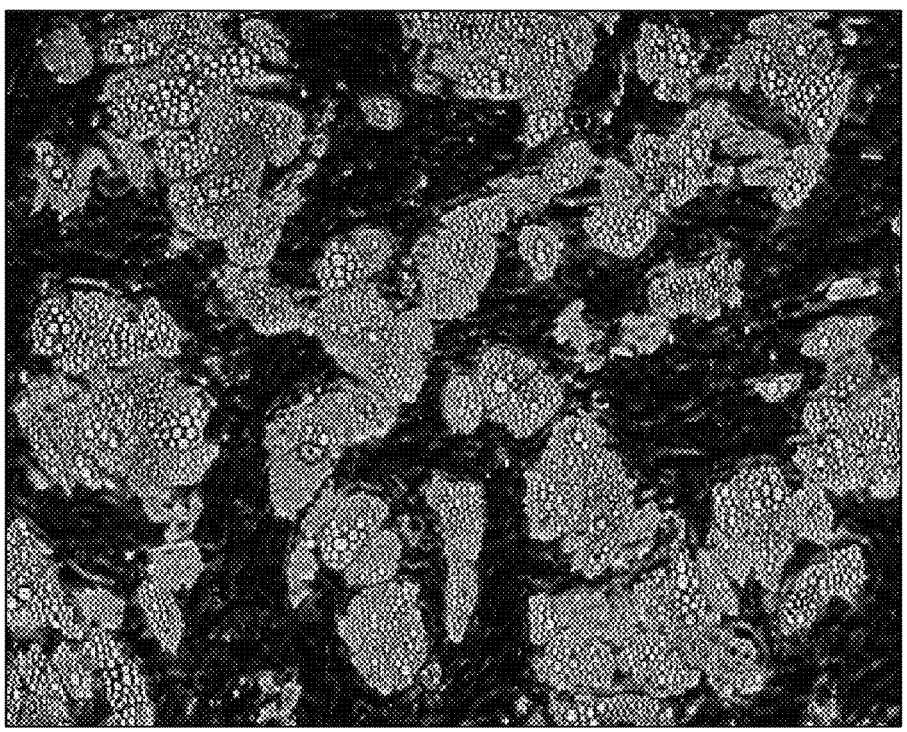

Mesenchymal Stem Cell (MSC) Attachment and Growth in Serum Free Media on ECM Coated Plasma Polymerized Surfaces Bone marrow derived MSCs (Lonza) were thawed and expanded on tissue culture flasks with complete MSC growth medium containing 10% serum (MSCGM™, Lonza). At passage 5, cells were dissociated with 0.5% trypsin EDTA, and plated on uncoated tissue culture plates with MSC growth medium containing serum (Lonza) (positive control; FIG. 9A) or on BD primex 1 plates coated with fibronectin in serum-free STEMPRO® MSC medium (Invitrogen) (FIG. 9B). After 5 days in culture, cell morphology and growth were visually inspected using a microscope. Typically attachment and growth of MSCs in serum-free medium is poor. In this example, it has been demonstrated that attachment of MSCs on BD Primex 1 plates coated with fibronectin is comparable to positive control conditions (cells grown on tissue culture surface with media containing serum).

Example 10

MSC Differentiation to Adipocytes on ECM Coated Plasma Polymerized Surfaces

Adipogenesis Culture Protocol

Adipogenic Induction Medium and Adipogenic Maintenance Medium were purchased from Lonza and manufacturer's protocol for adipogenesis was followed. 200,000 mesenchymal cells per well in 2 mL of medium were plated in 6 well tissue culture plates with serum containing growth media (MSCGM™, Lonza) or on fibronectin coated BD Primex 1 plates with serum-free MSC media (STEMPRO® MSC SFM; Invitrogen). Cells were Incubated at 37° C., in a humidified atmosphere of 5% CO2. Media was replaced on cells every 2 to 3 days until the cultures reached confluence (in ~7 days). At 100% confluence, three cycles of induction/maintenance were followed to stimulate adipogenic differentiation. Each cycle consisted of feeding the MSCs with Adipogenesis Induction Medium and cultured for 3 days (37° C., 5% CO2) followed by 1 to 3 days of culture in Adipogenic Maintenance Medium. After 3 complete cycles of induction/maintenance, the MSCs were cultured for 7 more days in Adipogenic Maintenance Medium, and medium was replaced every 2-3 days. The extent of adipogenic differentiation was visually inspected using a microscope to determine the presence of lipid vacuoles in the induced cells.

Results of MSC Differentiation to Adipocytes

The extent of adipogenesis on BD primex 1 plates coated with fibronectin (FIG. 9B) was similar to that observed on positive control tissue culture plates (FIG. 9A). This example illustrates that MSCs cultured with serum-free media on BD primex 1 plates coated with fibronectin retain their ability to differentiate into adipocytes and differentiation potential is comparable to that observed with positive control.

Example 11

NSC Growth and Attachment on ECM Coated Plasma Polymerized Surfaces

Human embryonic stem cell derived neuronal stem cells (hNSCs) were cultured in DMEM/F12 Media (1:1) supplemented with 2.5 mM L-Glutamine, 1% N2, 2% B27, 20 ng/mL bFGF and 1% Pen/Strep on tissue culture flasks coated sequentially with polyornithine followed by laminin.

To coat T-75 tissue culture flasks, 5 mL of polyornithine (20 µg/mL) dissolved in distilled water was added and flasks were laid flat to ensure the coating solutions evenly covered the bottom surface. Flasks were incubated overnight at room temperature. After 24 hours, the polyornithine solution was removed, the flask was rinsed once with distilled water and 5 mL of laminin (5 µg/mL) dissolved in Dulbecco's phosphate buffered saline was added. The bottom surface of the flask was coated with laminin and incubated at 37° C. for 2 hours. The coating solution was removed immediately prior to use for plating hNSCs.

In the present example, attachment and growth of hNSCs on ECM coated plasma polymerized surface was tested. Six well tissue culture and BD Primex 1 plates were coated with BD human fibronectin (25 µg/mL) for 2 hours at room temperature or a combination of polyornithine (20 µg/mL) and laminin (5 µg/mL) as described above. Tissue culture and BD PureCoat Amine plates (24 well) were coated with either polyornithine (20 µg/mL), laminin (5 µg/mL) or a combination of polyornithine (20 µg/mL) and laminin (5 µg/mL) as described above.

Figure 10A:
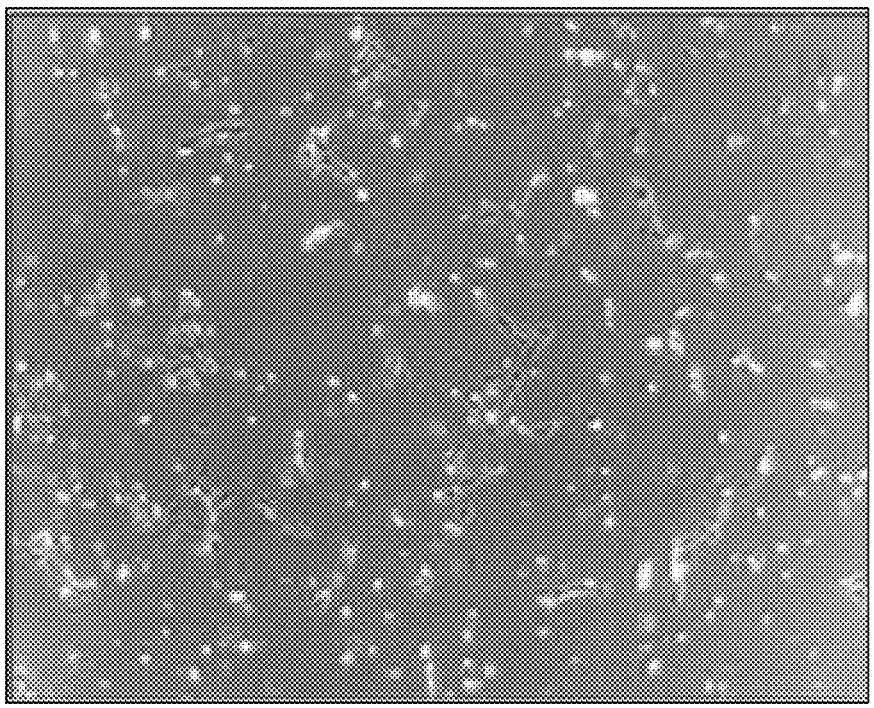
FIG. 10 Comparison of hES cell derived neuronal stem cell attachment and growth on tissue culture and plasma polymerized plates. Cells were seeded on uncoated tissue culture plates (FIG. 10a), tissue culture plates coated sequentially with polyornithine and laminin (FIG. 10b), uncoated plasma polymerized plates (FIG. 10c) and plasma polymerized plates coated with human fibronectin (FIG. 10d).
Figure 10B:
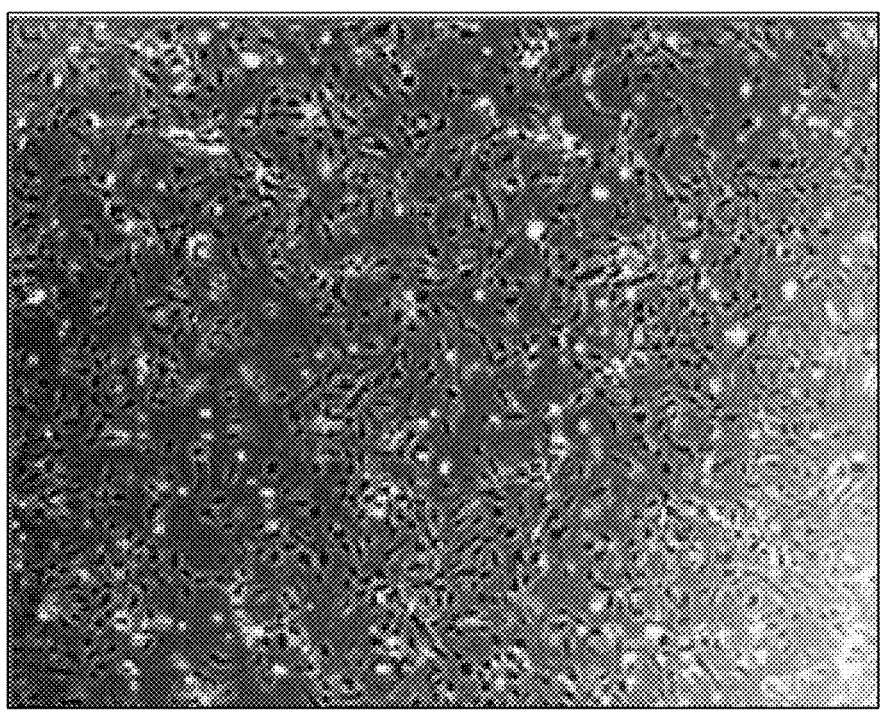
Figure 10C:
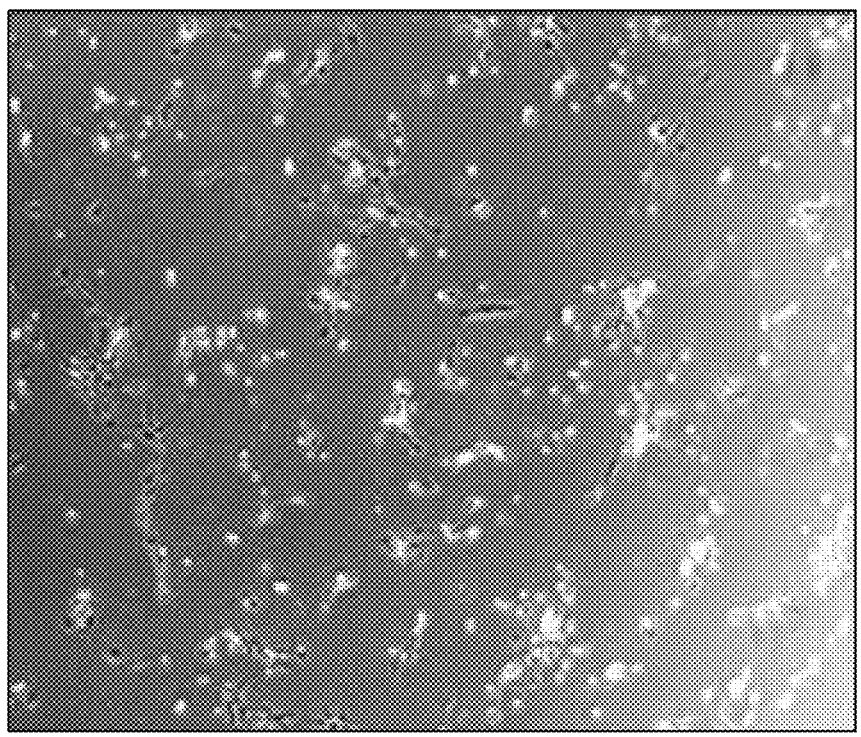
Figure 10D:
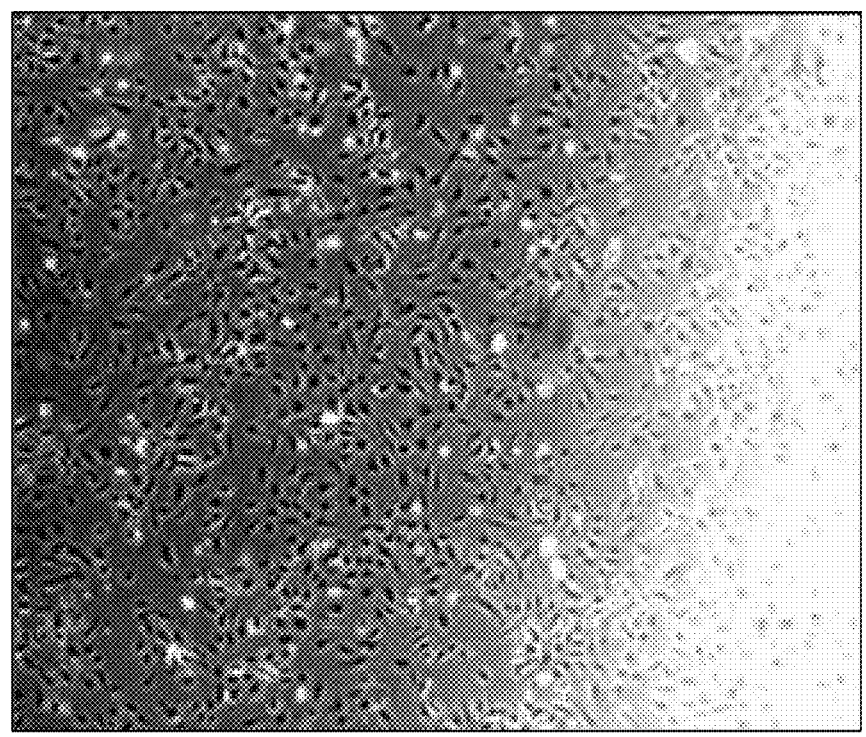

FIG. 10 illustrates that attachment and growth of hNSCs on BD primex 1 coated with fibronectin (FIG. 10d) is equivalent to tissue culture surface coated with a combination of polyornithine and laminin (positive control, FIG. 10b). Whereas, attachment and growth of hNSCs on uncoated tissue culture surface or BD Primex 1 is very low (FIGS. 10a and 10c respectively).

Figure 11:
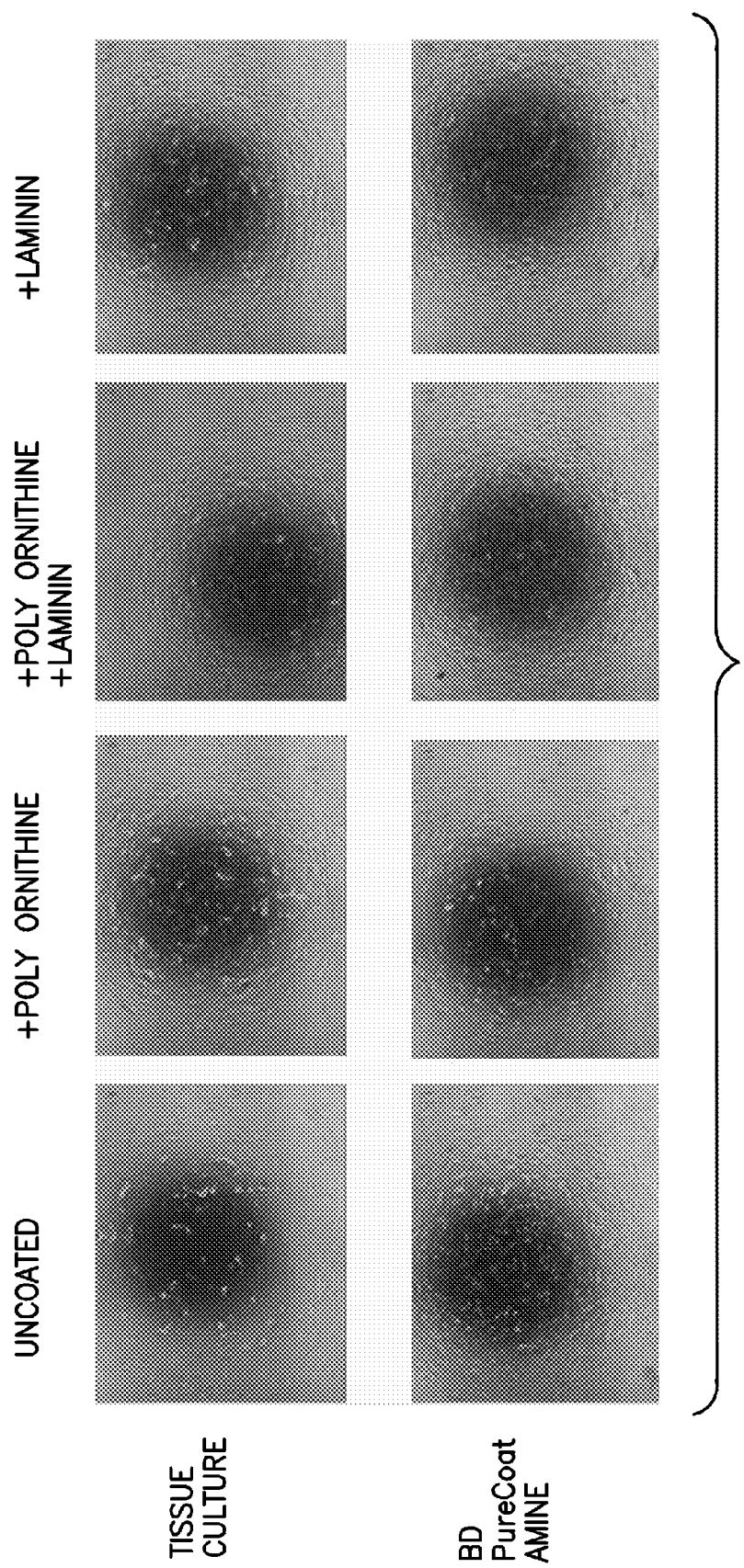
FIG. 11 Comparison of hES cell derived neuronal stem cell attachment and growth on tissue culture and plasma polymerized plates either uncoated or coated with various ECM proteins.

FIG. 11 illustrates that attachment and growth of hNSCs on BD PureCoat Amine coated with laminin (5 µg/mL) or a combination of polyornithine and laminin was better than tissue culture surface coated with the same ECMs.

Example 12

NSC Viability was Determined Using an MTS Assay

A tetrazolium-based assay was utilized to quantify cell viability. Briefly, exhausted media was removed, replaced with media containing MTS reagent (Promega), and incubated at 37° C. for 2 hours. MTS is a tetrazolium compound that is reduced by metabolically active living cells into a soluble product, formazan, that gives a purple hue. The absorbance of formazan at 490 nm was then read on a Tecan® Safire2™ microplate reader.

hNSCs were seeded at a density of 20,000 cells/well in 24 well BD PureCoat Amine plates where wells were either uncoated or coated with polyornithine, laminin or a combination of polyornithine and laminin. Three days later, spent medium was gently aspirated and replaced with 400 µL of flesh growth medium without bFGF. To each well, 80 µL of MTS reagent added and cells were incubated for 1.5 hours at 37° C. Absorbance was read at 490 nm.

Figure 12:
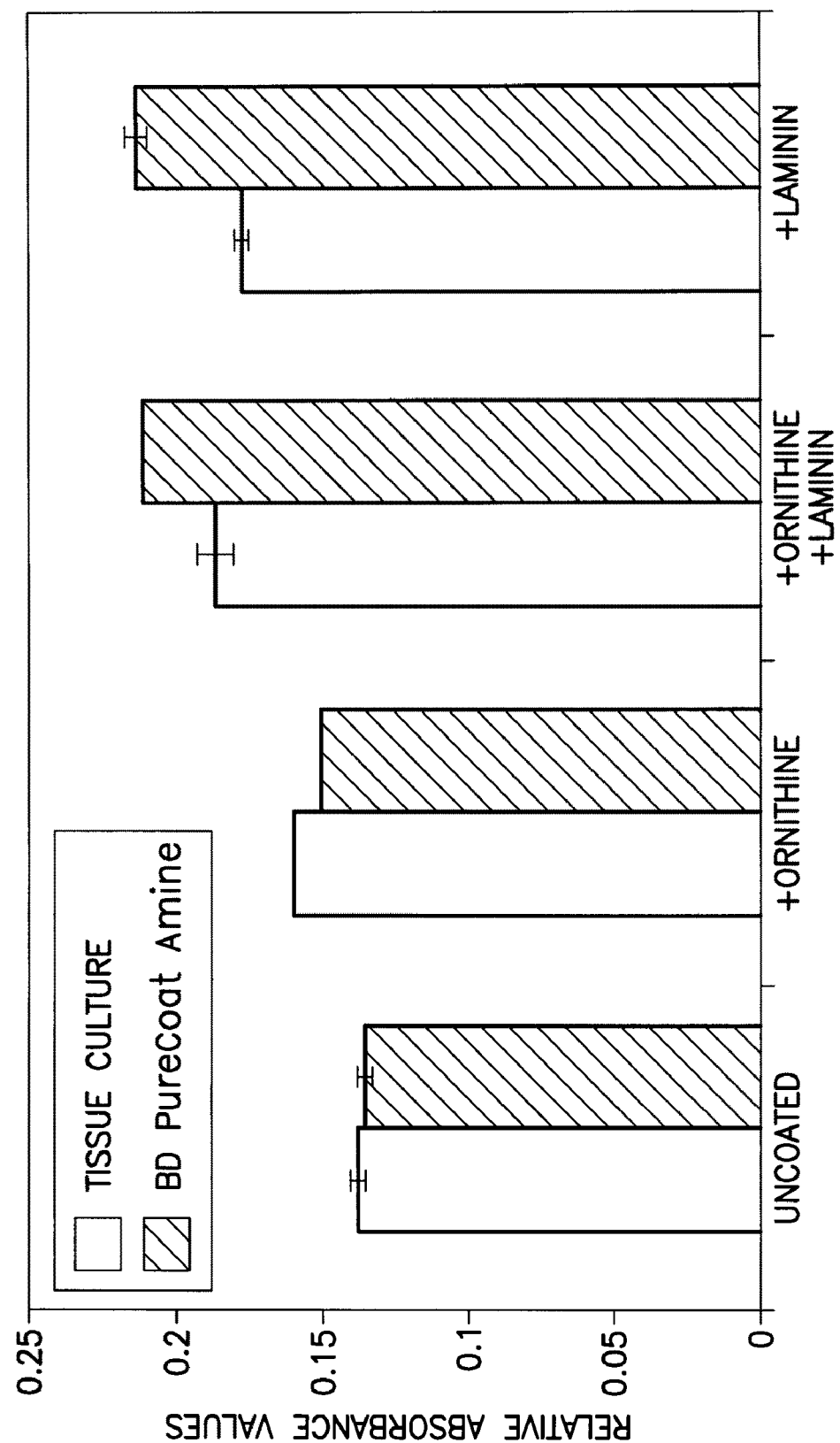
FIG. 12 This graph depicts cell viability of hES cell derived neuronal stem cell using an MTS assay.

Results of this experiment support the visual observations described in Example 8 (FIG. 12). hNSC viability on the BD PureCoat Amine surface was approximately 20 to 30% higher compared to tissue culture surface when coated with either laminin alone or with a combination of polyornithine and laminin. This example demonstrates that it is possible for hNSCs to attach, grow and remain viable on BD PureCoat Amine surface with a single ECM (laminin) and that it outperforms growth of these cells on tissue culture plates with two ECMs (polyornithine and laminin; positive control).

What is claimed is:

1. A method of preparing a cell culturing substrate comprising:
   providing a cell culture surface;
   plasma polymerizing a film onto said surface to form a film-coated surface, wherein said plasma polymerizing utilizes one or more monomers; and
   introducing a coating solution to said film-coated surface to form a cell culture substrate, said coating solution comprising one or more extracellular matrix proteins and an aqueous solution, wherein the total extracellular matrix protein concentration in the coating solution is about 1 ng/mL to about 1 mg/mL.

2. The method of claim 1, wherein said one or more monomers is selected from the group consisting of acrylic acid, methacrylic acid, acetic acid, vinylacetic acid and combinations thereof.

3. The method of claim 1, wherein said one or more monomers is selected from the group consisting of allylamine, methylamine, propylamine, heptylamine and diaminopropane.

4. The method of claim 1, wherein said one or more monomers is selected from the group consisting of alkanes, alkenes, dienes, styrenes and combinations thereof.

5. The method of claim 1, wherein said one or more monomers is selected from the group consisting of amines, hydrocarbons and combinations thereof, wherein the ratio of amine to hydrocarbon is between about 100:0 and about 20:80.

6. The method of claim 1, wherein the total extracellular matrix protein concentration in the coating solution is about 1 µg/mL to about 300 µg/mL.

7. The method of claim 1, wherein the total extracellular matrix protein concentration in the coating solution is about 5 µg/mL to about 200 µg/mL.

8. The method of claim 1, wherein the coating solution comprises extracellular matrix proteins selected from the group consisting of natural, recombinant, synthetic extracellular matrix proteins and combinations thereof.

9. The method of claim 1, wherein the coating solution comprises a whole extra cellular matrix protein or a fragment of the extracellular matrix protein.

10. The method of claim 1, wherein the coating solution further comprises a component selected from the group consisting of entactin, heparan sulfate proteoglycans (HSPG), growth factors and combinations thereof.

11. The method of claim 1, wherein the aqueous solution is selected from the group consisting of a buffer, a cell culture media and combinations thereof.

12. The method of claim 1, further comprising:
   incubating said cell culture substrate, wherein said one or more extracellular matrix proteins is immobilized on said film-coated surface.

13. The method of claim 1, farther comprising:
   freezing said cell culture substrate for a period of time, then incubating said cell culture substrate, wherein said one or more extracellular matrix proteins is immobilized on said film-coated surface.

14. The cell culturing substrate of claim 1, wherein one or more extracellular matrix proteins is a single type of extracellular matrix protein.

15. The cell culturing substrate of claim 1, wherein said extracellular matrix proteins are of human origin.

* * * * *